United States Patent
Duffy et al.

(10) Patent No.: US 11,801,134 B2
(45) Date of Patent: Oct. 31, 2023

(54) HEART VALVE DELIVERY CATHETER WITH SAFETY BUTTON

(71) Applicant: Medtronic, Inc., Minneapolis, MN (US)

(72) Inventors: Niall Duffy, Ballybrit (IE); John Gallagher, Ballybrit (IE); Kate Corish, Ballybrit (IE)

(73) Assignee: MEDTRONIC, INC., Minneapolis, MN (US)

( * ) Notice: Subject to any disclaimer, the term of this patent is extended or adjusted under 35 U.S.C. 154(b) by 541 days.

(21) Appl. No.: 17/015,491

(22) Filed: Sep. 9, 2020

(65) Prior Publication Data

US 2021/0052382 A1    Feb. 25, 2021

Related U.S. Application Data

(60) Continuation of application No. 15/657,680, filed on Jul. 24, 2017, now Pat. No. 10,799,352, which is a
(Continued)

(51) Int. Cl.
  *A61F 2/24* (2006.01)
  *A61F 2/966* (2013.01)
  *A61F 2/95* (2013.01)

(52) U.S. Cl.
  CPC ............ *A61F 2/2436* (2013.01); *A61F 2/966* (2013.01); *A61F 2/9517* (2020.05)

(58) Field of Classification Search
  None
  See application file for complete search history.

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| EP | 1980220 A | 10/2008 |
| EP | 1982677 A2 | 10/2008 |

(Continued)

OTHER PUBLICATIONS

PCT/US2011/023623, PCT International Search Report and Written Opinion, dated Jun. 7, 2011.

(Continued)

*Primary Examiner* — Shaun L David
(74) *Attorney, Agent, or Firm* — MEDLER FERRO WOODHOUSE & MILLS PLLC

(57) ABSTRACT

Valve delivery catheter assemblies including components that limit trauma to the expanded prosthetic valve and body channels as the distal tip of the catheter is withdrawn through the expanded valve and thereafter from the body. Catheter assemblies according to the present invention can include a handle assembly, an introducer sheath, and a distal tip assembly. The handle assembly can include a fixed main handle and two or more rotating handles that allow a user to control the distal tip assembly of the catheter. A safety button can be included on the handle assembly to allow for precise and consistent positioning of the prosthetic valve in the body. A valve retaining mechanism can be included to assist in retaining the prosthetic valve prior to deployment.

20 Claims, 23 Drawing Sheets

Related U.S. Application Data continuation of application No. 14/556,408, filed on Dec. 1, 2014, now Pat. No. 9,782,257, which is a division of application No. 13/016,658, filed on Jan. 28, 2011, now Pat. No. 8,926,693.

(60) Provisional application No. 61/305,488, filed on Feb. 17, 2010.

(56) References Cited

U.S. PATENT DOCUMENTS

| | | |
|---|---|---|
| 4,056,854 A | 11/1977 | Boretos et al. |
| 5,370,685 A | 12/1994 | Stevens |
| 5,545,214 A | 8/1996 | Stevens |
| 5,814,097 A | 9/1998 | Sterman et al. |
| 5,906,619 A | 5/1999 | Olson et al. |
| 2002/0004663 A1 | 1/2002 | Gitting et al. |
| 2003/0074045 A1 | 4/2003 | Buzzard et al. |
| 2003/0144731 A1 | 7/2003 | Wolinsky et al. |
| 2004/0193243 A1 | 9/2004 | Mangiardi et al. |
| 2005/0182475 A1 | 8/2005 | Jen et al. |
| 2006/0282150 A1 | 12/2006 | Olson et al. |
| 2007/0156224 A1 | 7/2007 | Cioanta et al. |
| 2007/0255390 A1 | 11/2007 | Ducke et al. |
| 2008/0262590 A1 | 10/2008 | Murray |
| 2010/0049313 A1 | 2/2010 | Alon et al. |

FOREIGN PATENT DOCUMENTS

| | | |
|---|---|---|
| FR | 9914462 | 11/1999 |
| WO | 93/01768 A1 | 2/1993 |
| WO | 97/28807 A1 | 8/1997 |
| WO | 2005/067819 A1 | 7/2005 |
| WO | 2008/138584 A1 | 11/2008 |
| WO | 2010/005524 A1 | 1/2010 |

OTHER PUBLICATIONS

Search report from counterpart European Patent Application No. 22161078.5, dated Aug. 3, 2022.

Communication of a Notice of Opposition issued Jan. 13, 2023 in European Appl. No. 11705084.9.

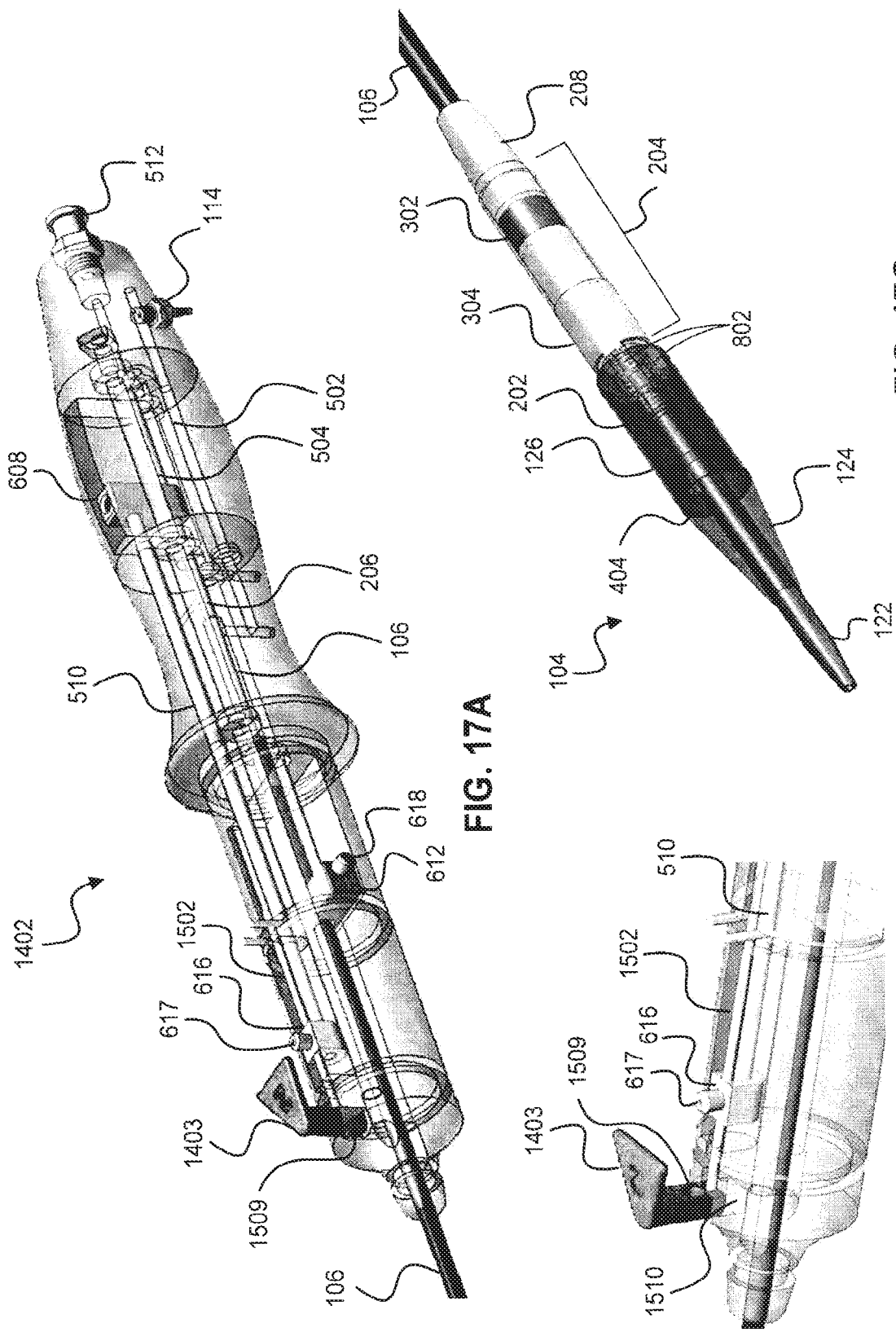

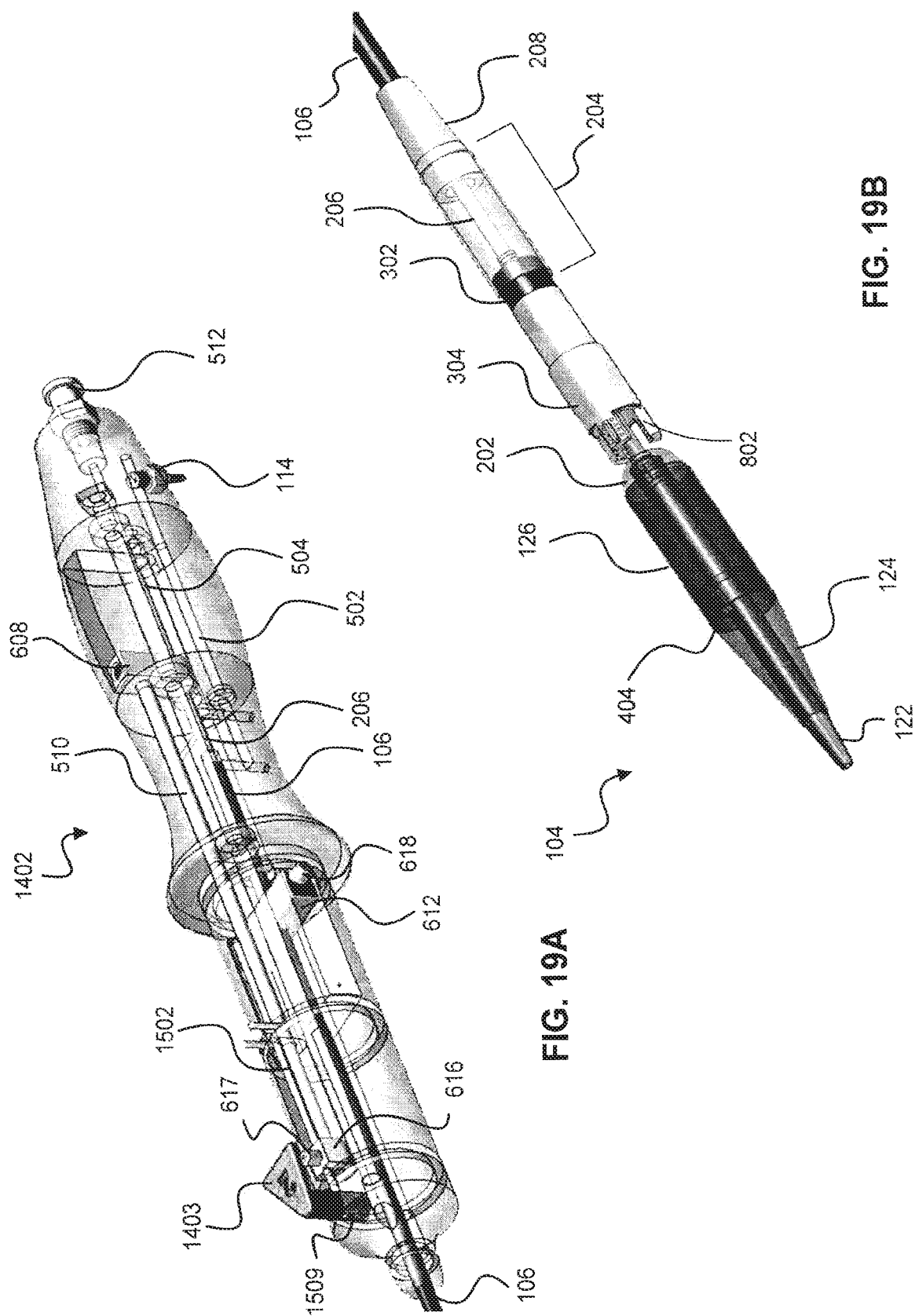

HEART VALVE DELIVERY CATHETER WITH SAFETY BUTTON

CROSS REFERENCE TO RELATED APPLICATIONS

This application is a continuation of prior U.S. patent application Ser. No. 15/657,680, filed Jul. 24, 2017, now U.S. Pat. No. 10,799,352, which is a continuation of prior U.S. patent application Ser. No. 14/556,408, filed Dec. 1, 2014, now U.S. Pat. No. 9,782,257, which is a divisional of prior U.S. patent application Ser. No. 13/016,658, filed Jan. 28, 2011, now U.S. Pat. No. 8,926,693, which claims benefit under 35 U.S.C. 119(e) to U.S. Provisional Patent Application 61/305,488, filed Feb. 17, 2010, each of which is incorporated by reference herein in its entirety.

BACKGROUND OF THE INVENTION

Field of the Invention

The present invention relates to heart valve delivery catheters and methods of delivering and implanting heart valves using delivery catheters. More specifically, the present invention relates to a delivery catheter with an improved handle design for controlling delivery of a heart valve via the catheter.

Background

Recently, minimally invasive approaches have been developed to facilitate catheter-based implantation of valve prostheses on the beating heart, intending to obviate the need for the use of classical sternotomy and cardiopulmonary bypass. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

U.S. Pat. No. 3,671,979 to Moulopoulos and U.S. Pat. No. 4,056,854 to Boretos describe catheter-mounted artificial heart valves for implantation in close proximity to a defective heart valve. Both of these prostheses are temporary in nature and require continued connection to the catheter for subsequent repositioning or removal of the valve prosthesis, or for subsequent valve activation.

With regard to the positioning of a replacement heart valve, attaching a valve on a support with a structure in the form of a wire or network of wires, forming a frame, has been proposed. This frame can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, frame-supported, tri-leaflet tissue heart valve that can be delivered through a portion of the vasculature using an elongate tool. The frame is mounted onto the expansion tool prior to delivery to the target location where the frame and valve are expanded into place.

Current techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter is transcatheterally advanced toward the native valve, where it is either forcefully deployed using a balloon catheter, or, alternatively, passively deployed using a self-expandable system. Accurate positioning of the replacement valve in the native annulus is critical to the success of the implantation. Although prior delivery catheter assemblies are sufficient to delivery a prosthetic valve to the native annulus, they do not provide a precise release mechanism for the valve such that error in placing the prosthetic valve in the native annulus is reduced.

The present invention provides a delivery catheter with an improved handle design for controlling delivery of a heart valve via the catheter. Delivery catheters according to embodiments of the present invention can include two or more rotatable control knobs on the catheter handle. These control knobs allows for accurate manipulation of the distal tip of the catheter. A safety button can be included on the catheter handle to further improve implantation accuracy. Delivery catheters according to embodiments of the present invention can also allow for further adjustment of the delivery position of a prosthetic valve retained by the distal tip of the catheter after a portion of the prosthetic valve has been exposed to the body channel.

BRIEF SUMMARY OF THE INVENTION

The catheter assemblies described herein seek to remedy one or more of the disadvantages of previous heart valve delivery catheters by providing catheters that allow for precise control of the release point of a prosthetic heart valve within the body. The catheter assemblies provided herein can also include components that limit trauma to the expanded prosthetic valve and body channels as the distal tip of the catheter is withdrawn through the expanded valve and thereafter from the body. In one embodiment, a catheter assembly according to the present invention includes a handle assembly, an introducer sheath, and a distal tip assembly. The handle assembly can include a fixed main handle and two or more rotating handles that allow a user to control the distal tip assembly of the catheter. The handle assembly can also include safety buttons to lock the rotating handles in a desired position corresponding to one stage of delivery. The distal tip assemblies described herein can include a slotted tip for breaching the apex of the heart during a transapical delivery approach. Distal tip assemblies may also include two or more sleeves for retaining a prosthetic valve prior to deployment of the prosthetic valve. A valve retaining mechanism can be included to assist in retaining the prosthetic valve prior to deployment. Each control knob on the handle assembly controls a portion of the components on the distal tip of the catheter by allowing for precise manipulation of various delivery shafts. A safety button can be included to allow for precise and consistent positioning of the prosthetic valve in the body. Each delivery shaft extends from the handle assembly to respective positions towards the distal end of the catheter. Preferably, rotating one of the control knobs causes a distal sleeve on the distal tip of the catheter to move in a distal direction, thereby at least partially releasing a prosthetic valve. Rotating a second one of the control knobs can cause a proximal sleeve on the distal tip of the catheter to move in a proximal direction, thereby fully releasing a self-expanding prosthetic valve at a desired location in the body. Once the valve is deployed, the catheter can be withdrawn from the body.

BRIEF DESCRIPTION OF THE FIGURES

The accompanying figures, which are incorporated herein, form part of the specification and illustrate embodiments of heart valve delivery catheters and methods of delivering and implanting heart valves using delivery catheters. Together with the description, the figures further serve to explain the principles of and to enable a person skilled in the relevant art(s) to make and use the delivery catheters and methods of using delivery catheters described herein. In the drawings, like reference numbers indicate identical or functionally similar elements.

FIGS. 17A and 17B illustrate a delivery catheter handle and distal tip assembly of a delivery catheter according to one embodiment of the present invention at a second stage of delivery. FIG. 17C illustrates in more detail the features of the support arm release button and related components.

FIGS. 19A and 19B illustrate a delivery catheter handle and distal tip assembly of a delivery catheter according to one embodiment of the present invention at a fourth stage of delivery.

DETAILED DESCRIPTION OF THE INVENTION

The following detailed description of heart valve delivery catheters and methods of delivering and implanting heart valves refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided is directed to catheters for transapical delivery of a heart valve, the catheters and individual features of the catheters described herein should not be limited to transapical delivery of a heart valve. One of skill in the art would readily understand how to incorporate the features and structures described herein into catheters intended for other purposes. For example, features of the catheters described herein can be incorporated into catheters intended for other types of transluminal heart valve delivery as well as catheters intended for thorascopic heart valve delivery. Features of the catheters described herein can also be incorporated into catheters designed for delivery of stents or valves to areas of the body other than the heart.

Figure 1:
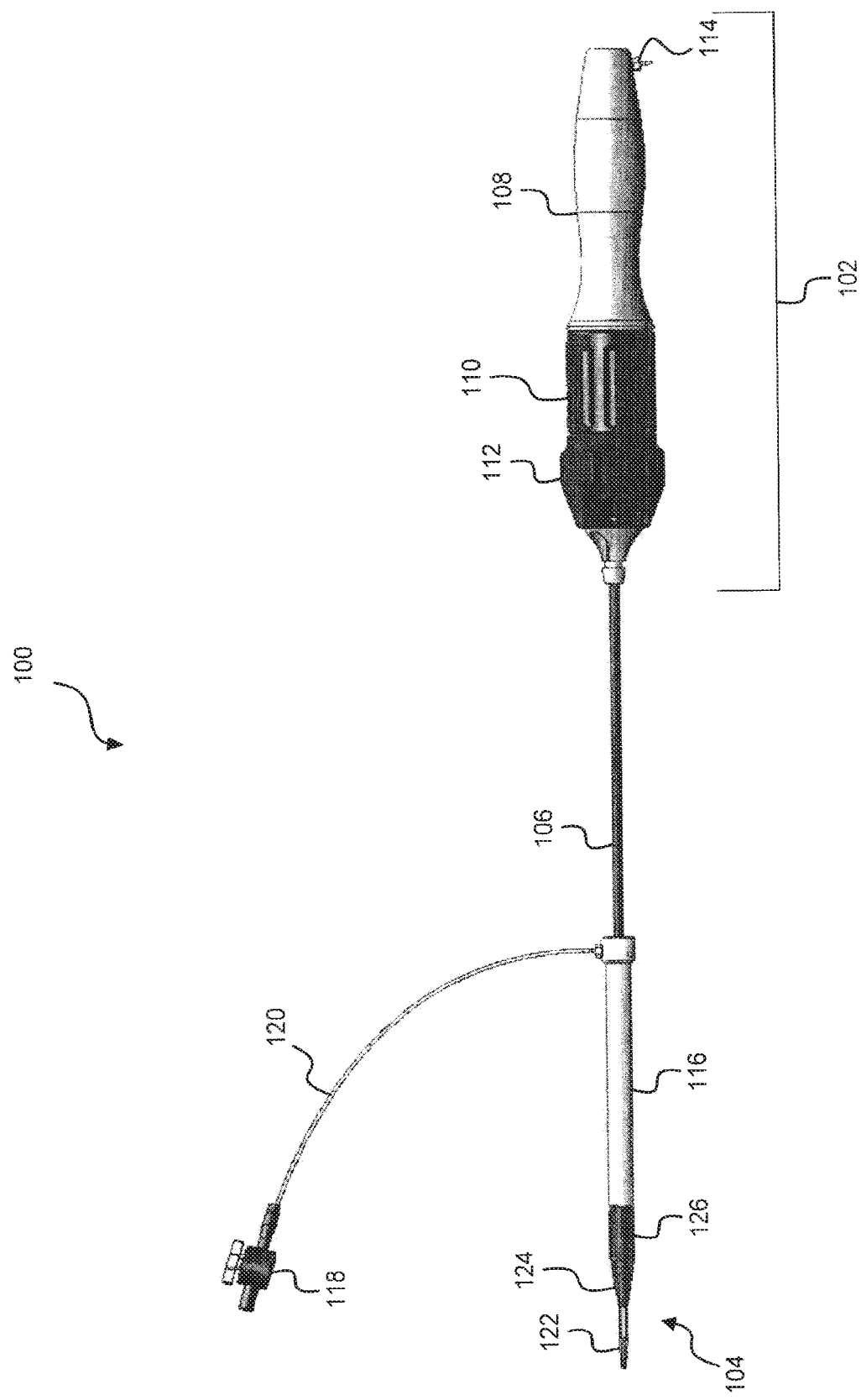
FIG. 1 illustrates a closed catheter assembly in accordance with one embodiment presented herein.

FIG. 1 illustrates a catheter assembly 100 in accordance with one embodiment presented herein. Catheter assembly 100 is depicted in FIG. 1 in a closed configuration. Catheter assembly 100 generally includes a handle assembly 102 located at the proximal end of the catheter, a distal tip assembly 104 located at the distal end of the catheter, and an introducer 116 slidably located along a outer delivery shaft 106 between the distal tip assembly 104 and the handle assembly 102.

Outer delivery shaft. 106 is preferably a tubular flexible braided structure. Outer delivery shaft 106 can be formed of braided material fabricated from materials such as, but not limited to, polyethylene naphthalate (PEN), polyester (PET), stainless steel, titanium, nitinol, cobalt nickel alloy, polyimide, polyimide, or the like. In some embodiments, outer delivery shaft may contain reinforcing materials or structures. These structures can include an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of a polymeric material. In other embodiments, the inner layer of polymeric material is overlaid by a braided layer, which is overlaid by the coil winding, which is overlaid by another layer of braid, which is in turn overlaid by an outer polymeric layer. Preferably, however, any reinforcing layer used allows outer delivery shaft 106 to retain a degree of flexibility. Other flexible materials can also be used to form outer delivery shaft 106 consistent with embodiments of the present invention.

Handle assembly 102 includes a main handle 108, a proximal control knob 110, and a distal control knob 112. Main handle 108, a proximal control knob 110, and distal control knob 112 can be formed of any suitable material. For example, in some embodiments the handle and control knobs are formed of a polymer material. Other materials are possible, as would be understood in the art. A flushing port 114 can also be included on main handle 108. Flushing port 114 can be used to de-air the catheter assembly. Also, the native annulus is exposed to the blood pressure in a patient's cardiovascular system during use of a heart valve delivery catheter. As a consequence, in the absence of any counter pressure in this annulus, blood can flow inside towards the proximal end of the catheter, where it may coagulate and cause thrombosis. Thus, flushing port 114 can also allow fluid to be introduced into the native annulus to prevent such complications. In some embodiments, flush port 114 can also be used for site specific drug delivery or to introduce radiopaque fluid into the body.

As will be described herein, proximal control knob 110, and distal control knob 112 can be manipulated by a user in order to control operation of the distal tip assembly 104 of catheters described herein. A detailed description of the operation and structure of handle assembly 102 is provided below, particularly with reference to FIGS. 5-10. Distal tip assembly 104 includes a tip 122, which is preferably slotted for the reasons described herein, a tip connector 124, and a support arm sleeve 126. A flushing tap 118 and a flushing tap lead 120 can be connected to an introducer 116. Introducer 116 is preferably a tubular member that is slidably located over outer delivery shaft 106. Introducer 116 may be formed of a variety of materials, for example, stainless steel or various polymer materials. A detailed description of the operation and structure of distal tip assembly 104 and introducer 116 is provided below, particularly with reference to FIGS. 2-4 and 8-12. Catheter 100 is configured to be advanced along a guide wire (not shown). Preferably, the catheter is advanced over a 0.035 inch guide wire. However, the dimensions of the catheter components can be adjusted for advancement over guide wires with larger or smaller diameters.

Figure 2:
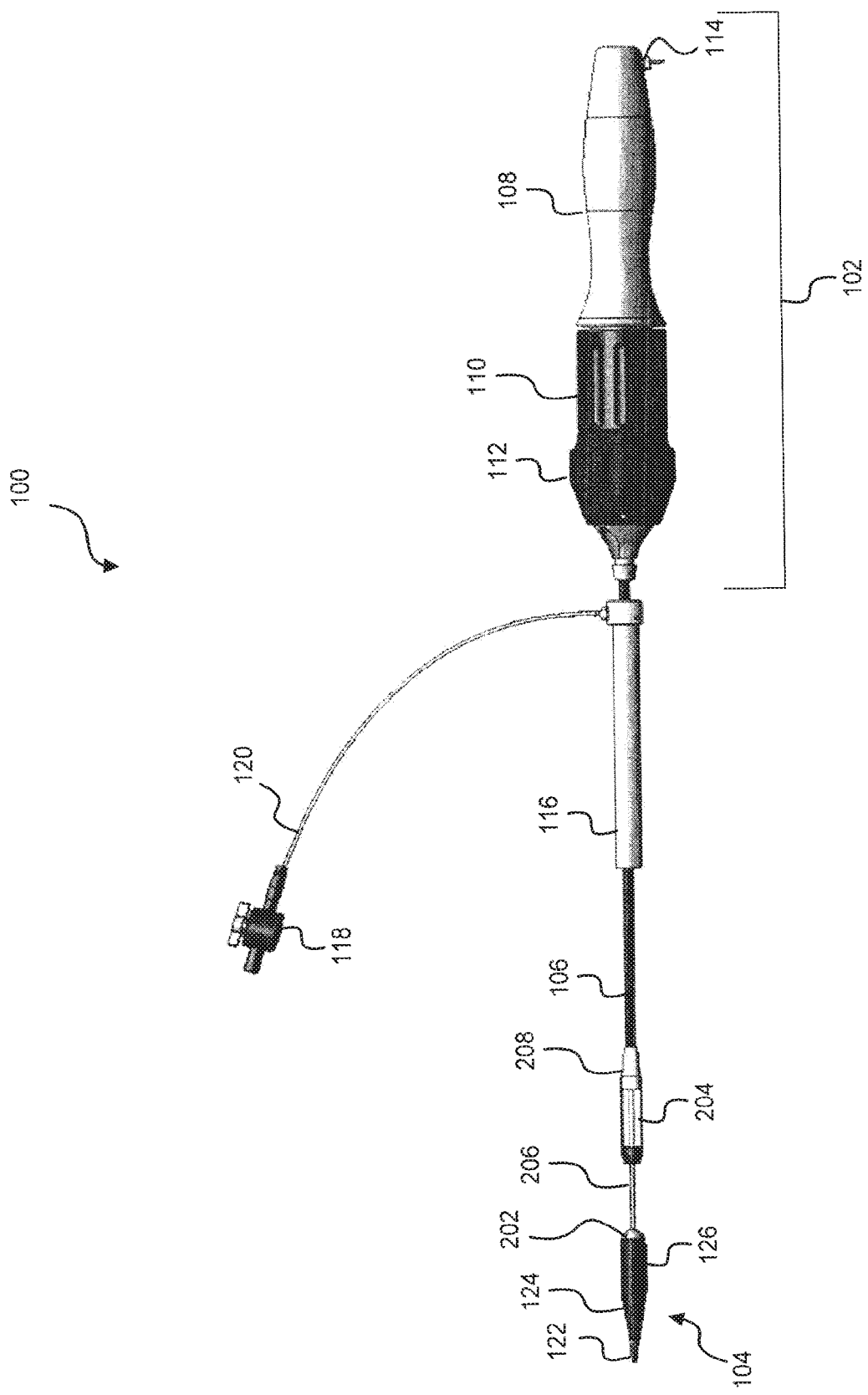
FIG. 2 illustrates the catheter assembly of FIG. 1 in an open configuration.

FIG. 2 illustrates catheter assembly 100 in an open configuration. Catheter assembly 100 reaches the open configuration when introducer 116 is moved proximally along outer delivery shaft 106 to expose a valve retaining sleeve 204, a valve retaining sleeve connector 208, and semi-sphere 202 of distal tip assembly 104. Valve retaining sleeve connector 208 secures valve retaining sleeve 204 to the distal end of the outer delivery shaft 106. The outer delivery shaft 106 therefore extends from the interior of handle assembly 102 to sleeve connector 208. Slotted tip 122 and semi-sphere 202 are positioned on and connected to the distal end of an intermediate delivery shaft 206. Intermediate delivery shaft 206 extends from the interior of handle assembly 102 to slotted tip 122, to which the distal end of intermediate delivery shaft 206 is attached. Intermediate delivery shaft 206 is encompassed by outer delivery shaft 106 from the interior of handle assembly 102 until the outer delivery shaft 106 ends at sleeve connector 208. Semi-sphere 202 is attached to the proximal end of slotted tip 122. In one embodiment, semi-sphere 202 can be attached directly to intermediate shaft 206. Intermediate shaft 206 is preferably a tubular member.

A guide wire shaft 504 (shown in FIG. 5) is encompassed within intermediate shaft 206 and extends from the inside of handle assembly 102 to the proximal end of slotted tip 122. Thus, in one embodiment of the present invention, at least three shafts extend from the main handle, and the shafts are nested along at least a part of their lengths. Specifically, guide wire shaft 504 is encompassed by the intermediate delivery shaft 206 from a position inside of handle assembly 102 to the interior of slotted tip 122, which is preferably hollow through at least a portion thereof. Intermediate delivery shaft 206 is connected to, and ends, at the proximal end of slotted tip 122. In turn, intermediate delivery shaft 206 is encompassed by the outer delivery shaft 106 from a position inside of handle assembly 102 to the valve retaining sleeve connector 208. Outer delivery shaft 106 is connected to, and ends, at the retaining sleeve connector 208. Intermediate shaft 206 and guide wire shaft 504 can be constructed of various polymer materials, and may be braided structures using materials described above with reference to outer delivery shaft 106.

Figure 3:
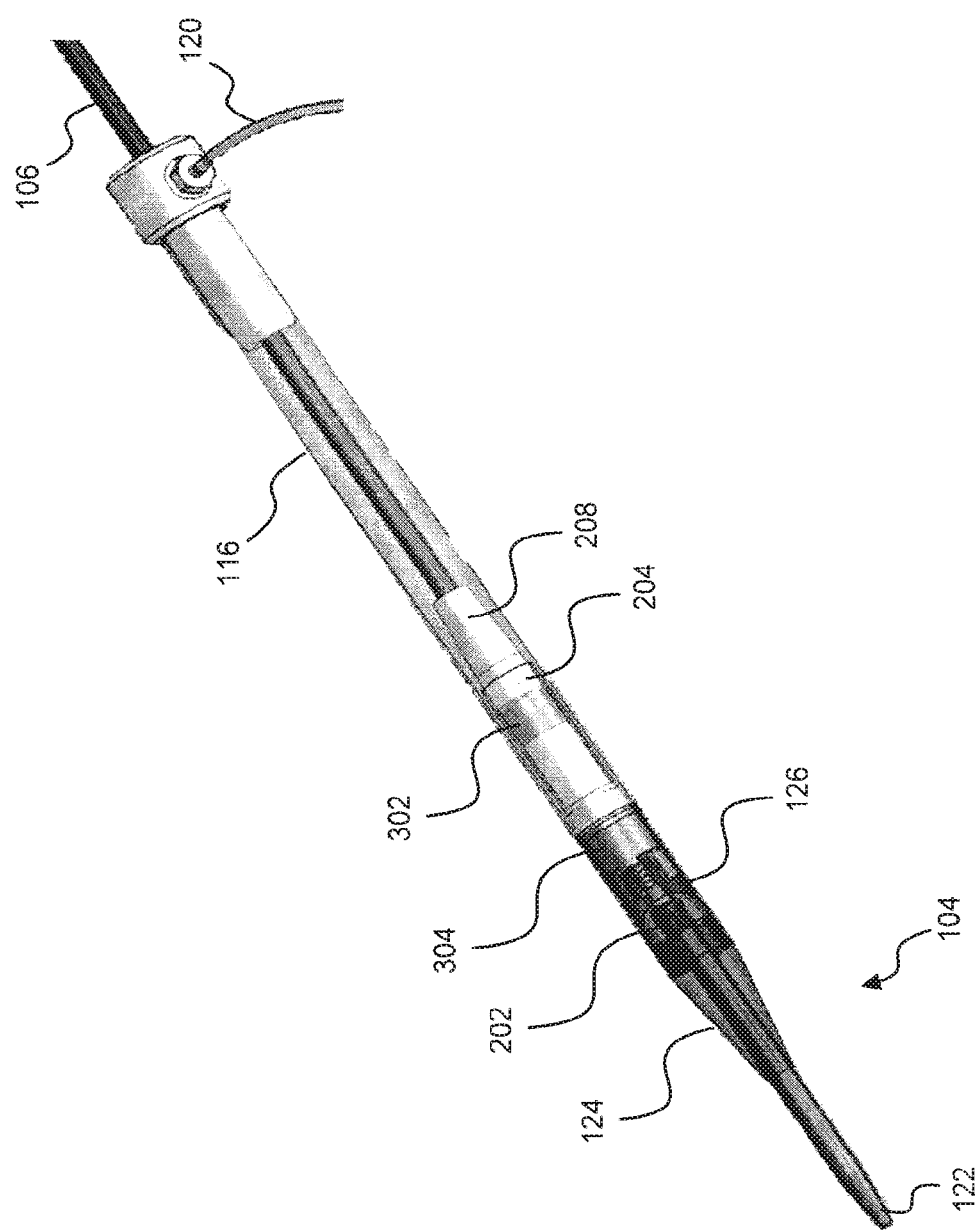
FIG. 3 is a depiction of the distal tip assembly and introducer of a catheter according to one embodiment of the present invention in a closed configuration.

FIG. 3 is a depiction the distal tip assembly 104 and introducer 116 of a catheter according to one embodiment of the present invention in a closed configuration. Introducer 116, valve retaining sleeve 204, support arm sleeve 126, and tip connector 124 are rendered transparent in FIG. 3 in order to facilitate description of certain components. Tip connector 124 is slidably positioned over the proximal end of slotted tip 122, as will be detailed below with reference to FIG. 4. The distal end of intermediate delivery shaft 206 is connected to slotted tip 122. A simplified rendering of a prosthetic heart valve 304 is shown attached to a valve retainer 302. Valve retainer 302 is also connected to intermediate delivery shaft 206. Valve retainer 302 serves to retain prosthetic valve 304 in place during delivery to the desired location within a patient. Valve retainer 302 can be made from a polymer or metal material suitable for exposure to a patient's circulatory system. Prosthetic valve 304 preferably has a frame that is formed from a self-expanding material, for example, Nitinol. This material allows the structure to be contracted radially at a temperature different from that of the body of the patient and to regain its original expanded shape when its temperature approaches or reaches that of the body of the patient. The valve portion of prosthetic valve 304 can be made of biological tissue, such as bovine or porcine pericardium, or from synthetic materials. When in a closed configuration, at least a portion of prosthetic valve 304, and valve retainer 302, are encompassed by valve retaining sleeve 204, and valve retaining sleeve 204 is in turn encompassed by introducer 116. In this configuration, the distal end of introducer 116 abuts the proximal end of support arm sleeve 126.

Figure 4:
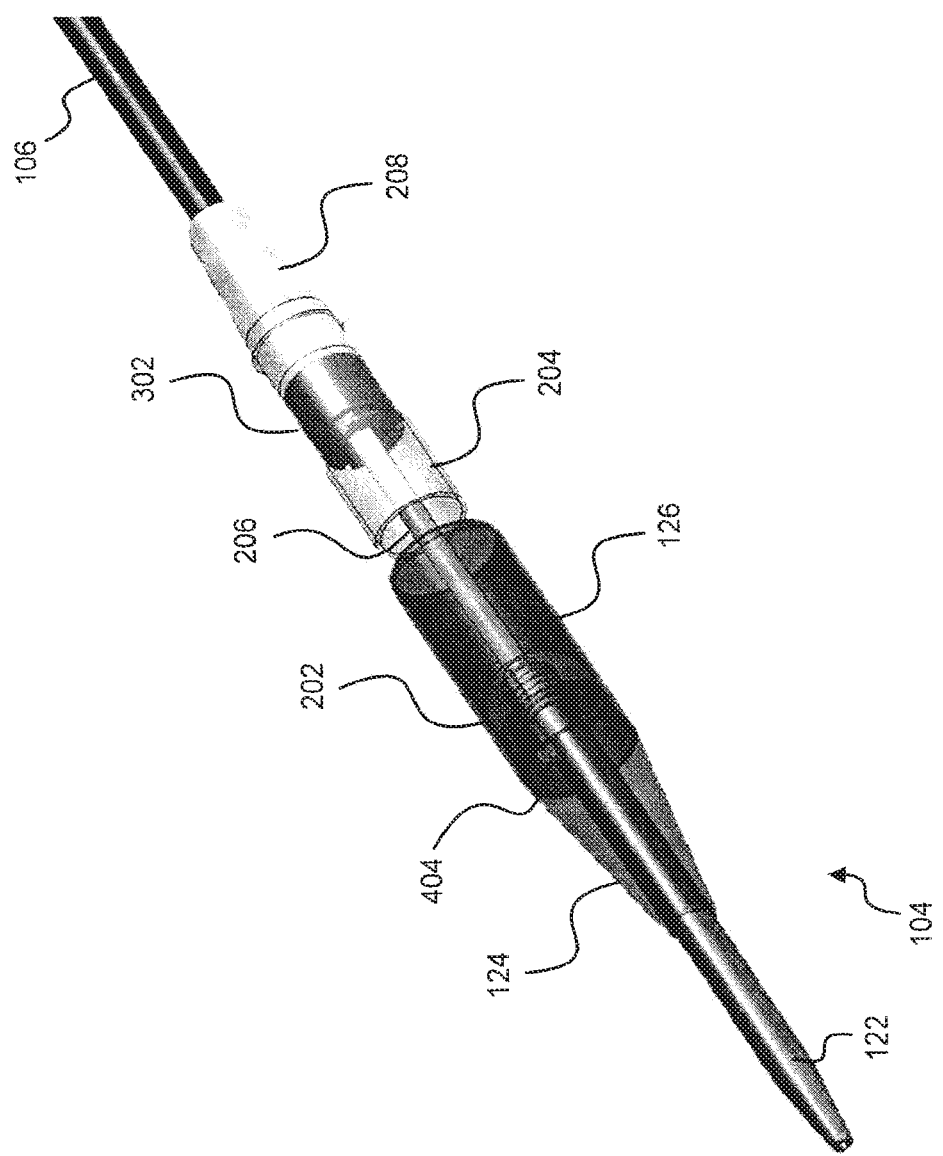
FIG. 4 illustrates the distal tip and introducer assemblies of a catheter in accordance with one embodiment presented herein in a partially open configuration.

FIG. 4 illustrates the distal tip assembly 104 of a catheter in accordance with one embodiment presented herein in a partially open configuration. As shown in FIG. 4, tip connector 124 is affixed to the guide wire shaft 504 (not shown in FIG. 4) via a connecting fin 404. Connecting fin 404 is attached to the distal end of guide wire shaft 504. An axial slot (not shown) in slotted tip 122 allows the connecting fin 404 to slide axially along slotted tip 122 when guide wire shaft 504 is moved in a distal direction. As noted above, slotted tip 122 is affixed to the distal end of intermediate delivery shaft 206. The proximal end of intermediate delivery shaft 206 is preferably fixed in a stationary position inside handle assembly 102. Thus, slotted tip 122 and semi-sphere 202, which is preferably connected to slotted tip 122, are held in a fixed position by intermediate delivery shaft 206 when guide wire shaft 504 is moved in an axial direction. In one embodiment, tip connector 124 is affixed to connecting fin 404 by over-molding the tip connector 124 around the connecting fin 404. It is understood that tip connector 124 can be affixed to fin 404 by any one of several suitable methods, such as a tongue and groove assembly, gluing, etc. The distal end of support arm sleeve 126 is connected to the proximal end of tip connector 124 so that the support arm sleeve 126 and tip connector 124 move together. In the configuration shown in FIG. 4, intermediate delivery shaft 206 has been advanced distally while outer delivery shaft 106 is retained in a fixed position.

Figure 5:
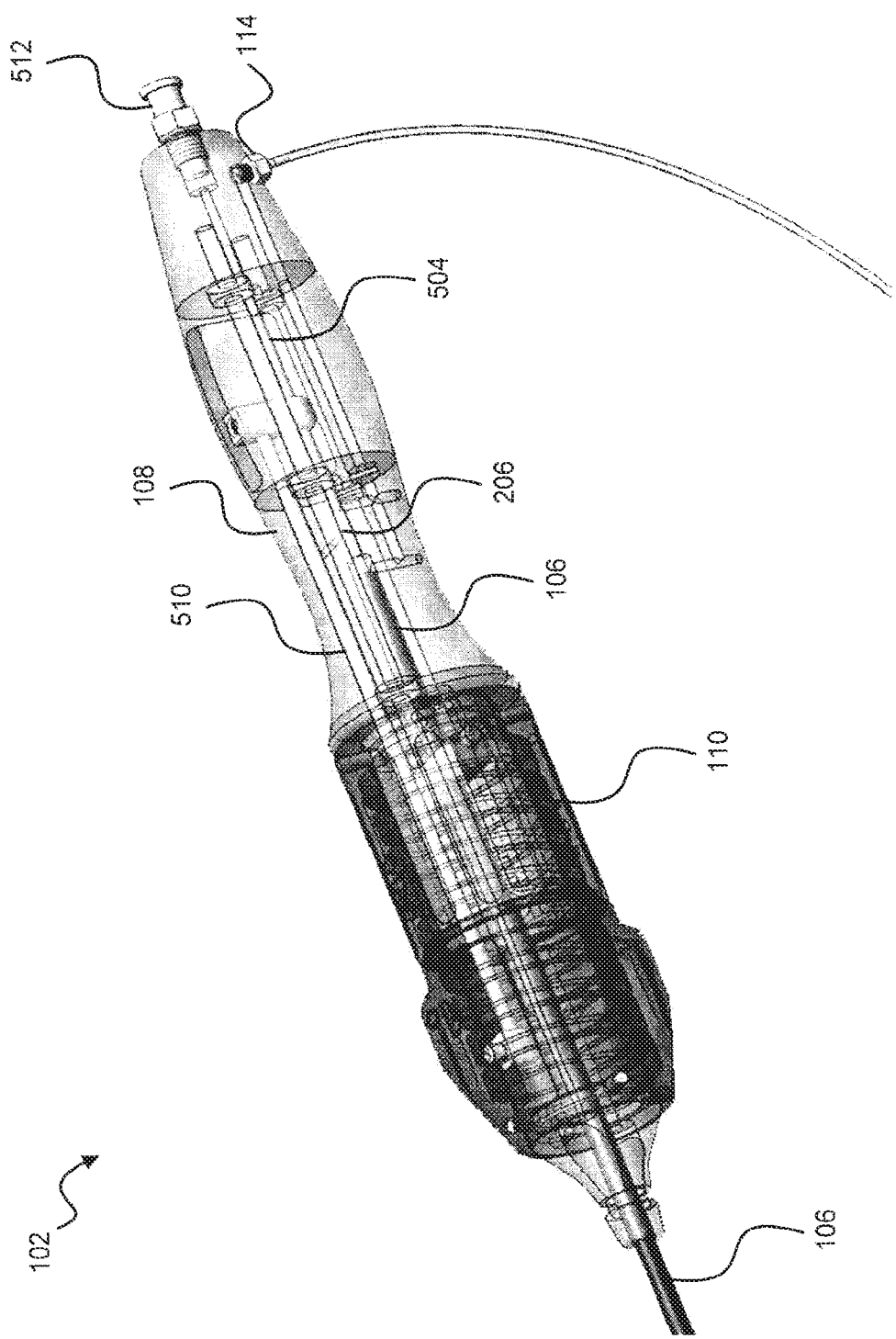
FIG. 5 illustrates a delivery catheter handle in accordance with one embodiment presented herein.
Figure 6:
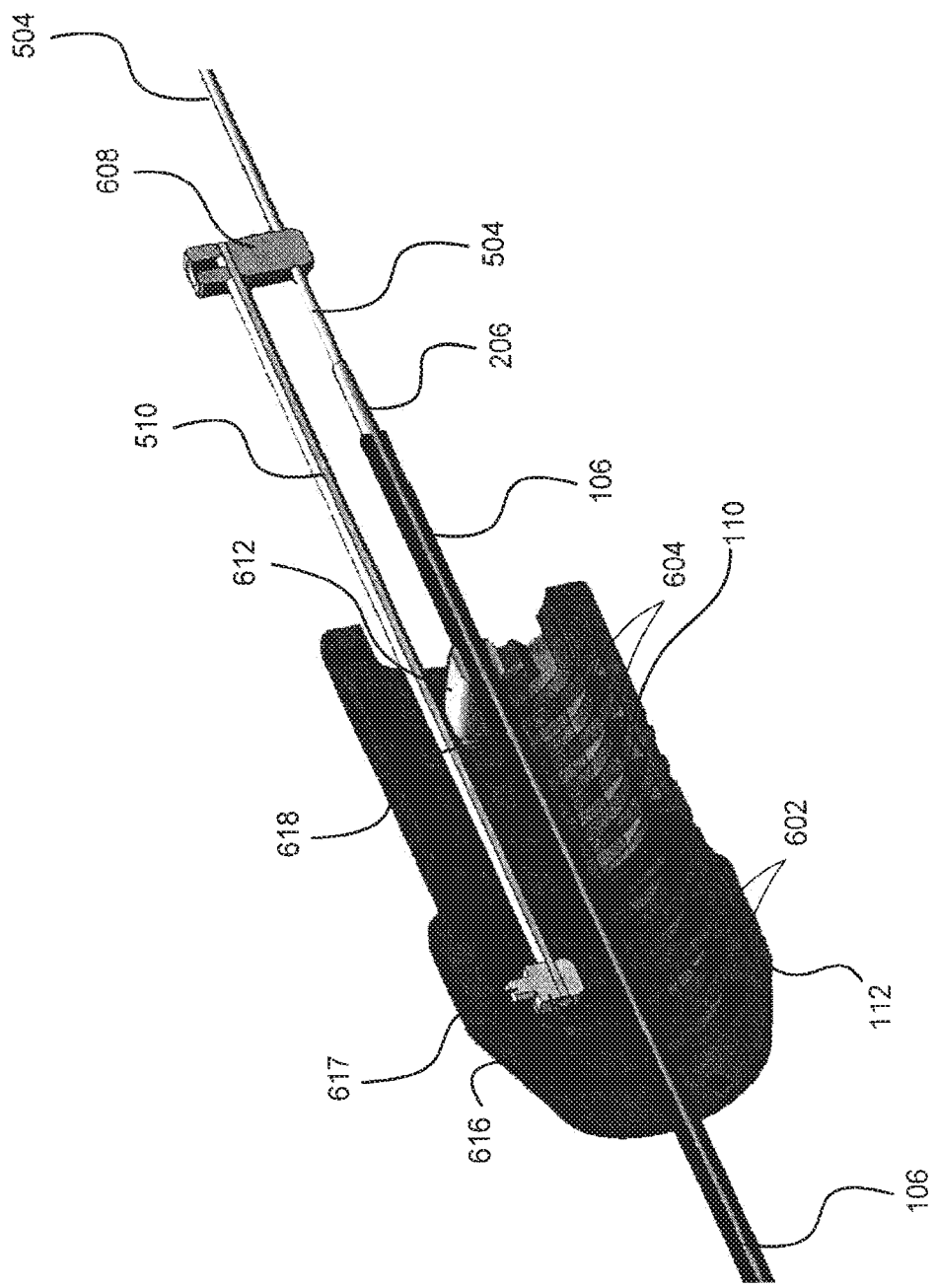
FIG. 6 illustrates a simplified interior of a delivery catheter handle in accordance with one embodiment of the present invention.
Figure 7:
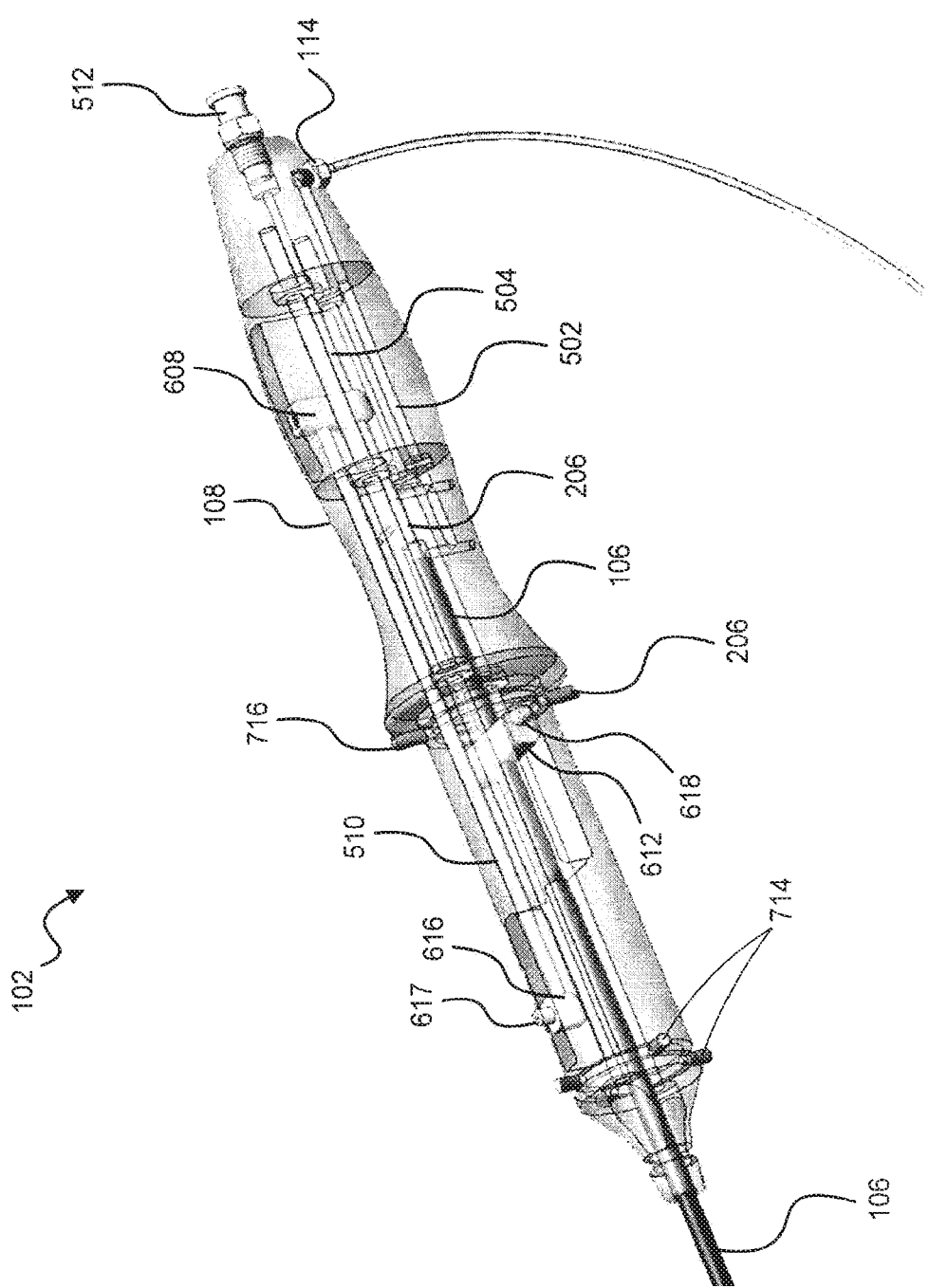
FIG. 7 illustrates a second simplified view of a portion of a delivery catheter handle in accordance with one embodiment of the present invention.

FIG. 5 illustrates a delivery catheter handle assembly 102 in accordance with one embodiment presented herein. Handle assembly 102 includes a main handle 108, a rotatable proximal control knob 110, and a rotatable distal control knob 112. The handle sections of handle assembly 102 are preferably connected using O-rings (not shown). As seen in FIG. 7, knob pins 714 on the distal end of handle assembly 102 locate distal control knob 112 on handle assembly 102. A circular channel (not shown) is formed on the interior surface of distal control knob 112, and the channel receives knob pins 714, thereby preventing movement of distal control knob 112 in an axial direction while permitting rotation of distal control knob 112 around the longitudinal axis of handle assembly 102. Alternately, circular channels can be formed on handle assembly 102 and control knobs 110 and 112 can include inwardly projecting tabs or inwardly projecting ridges configured to mate with the circular channels to prevent axial movement of the knobs. Knob pins 716 located under the proximal end of proximal control knob 110 locate proximal control knob 110 on handle assembly 102. A circular channel (not shown) is formed on the interior surface of proximal control knob 110, and the channel receives knob pins 716, thereby preventing movement of proximal control knob 110 in an axial direction while permitting rotation of proximal control knob 110 around the longitudinal axis of handle assembly 102. It is understood that the handle sections can be connected using other mechanisms that would allow movement of the sections relative to each other. Other structures can be used to secure control knobs 110 and 112 to handle assembly 102 to prevent axial movement thereof. For example, circular ridges can be provided in handle assembly 102 in place of pins 714 and 716 in order to mate with the circular grooves formed on the interior surfaces of knobs 110 and 112. A ratchet system can also be used to rotatably secure control knobs 110 and 112 to handle assembly 102. Both proximal control knob 110 and distal control knob 112 are threaded on their interior surfaces, as shown in further detail in FIG. 6. The configuration of the handle assembly 102 allows a user to precisely control the movement of the guide wire shaft 504 and the outer delivery shaft 106, and thereby manipulate the components of distal tip assembly 104. As shown in FIGS. 5-7 handle assembly 102 includes a distal guide wire shaft boss 616 configured to engage the inner threads 602 of the distal control knob 112. Specifically, distal guide wire shaft boss 616 preferably has a tongue 617 that engages inner threads 602 of distal control knob 112. Inner threads 602 are formed such that, as distal control knob 112 is rotated in a clockwise direction by a user, distal guide wire shaft boss 616 is forced in a distal direction, that is, towards the distal end of handle assembly 102. Distal guide wire shaft boss 616 is connected to proximal guide wire shaft boss 608 by connecting bar 510. Proximal guide wire shaft boss 608 is connected to guide wire shaft 504, Therefore, in operation, clockwise rotation of distal control knob 112 moves distal guide wire shaft boss 616 towards the distal end of handle assembly 102. Because distal guide wire shaft boss 616 is coupled to guide wire shaft 504 through connecting bar 510 and proximal guide wire shaft boss 608, guide wire shaft 504 moves in a distal direction when distal guide wire shaft boss 616 moves in a distal direction. Although a specific manner of connecting distal guide wire shaft boss 510 to guide wire shaft 504 is described above, it is understood that in other embodiments of the present invention, alternate mechanisms can be used to ensure that rotation of distal control knob 112 results in axial movement of guide wire shaft 504.

Handle assembly 102 further includes an outer delivery shaft boss 612 configured to engage the inner threads 604 of the proximal control knob 110. Specifically, outer delivery shaft boss 612 preferably has a tongue 618 that engages inner threads 604 of proximal control knob 110. Outer delivery shaft boss 612 is connected to outer delivery shaft 106. In operation, counter-clockwise rotation of proximal control knob 110 moves outer delivery shaft boss 612 towards the proximal end of handle assembly 102. Because outer delivery shaft boss 612 is coupled to outer delivery shaft 106, outer delivery shaft 106 moves in a proximal direction when proximal control knob 110 moves in a proximal direction. Although a specific manner of connecting outer delivery shaft boss 612 to outer delivery shaft 106 is described above, it is understood that in other embodiments of the present invention, alternate mechanisms can be used to ensure that rotation of outer delivery shaft boss 612 results in axial movement of outer delivery shaft 106.

Handle assembly 102 also includes an intermediate delivery shaft 206. Intermediate delivery shaft 206 is fixedly secured to the inside of main handle 108, preferably by an O-ring. It is understood that intermediate delivery shaft 206 can be secured to main handle 108 by other methods, for example, by welding, bolting, over-molding, etc. Guide wire shaft 504 is encompassed by, but not affixed to, intermediate delivery shaft 206 such that guide wire shaft 504 is axially movable with respect to intermediate delivery shaft 206. Intermediate delivery shaft 206 is encompassed by, but not affixed to, outer delivery shaft 106 such that outer delivery shaft 106 is axially movable with respect to intermediate delivery shaft 206. The entire catheter assembly 100 can be placed over a pre-positioned guide wire (not shown) by sliding guide wire shaft 504 over the guide wire and out of guide wire port 512. Guide wire port 512 can also be used as a supplemental flushing port. Handle assembly 102 further includes a flushing channel 502 located within main handle 108. Flushing channel 502 is fluidly connected to the space between outer delivery shaft 106 and intermediate delivery shaft 206 and the space between intermediate delivery shaft 206 and guide wire shaft 504. Flushing channel 502 is fluidly connected to flushing port 114. In some embodiments, flushing channel 502 is fluidly connected to guide wire port 512 in addition to, or instead of, flushing port 114.

At the beginning of a procedure distal guide wire shaft boss 616 is positioned towards the distal end of handle assembly 102, near distal control knob pins 714, and outer delivery shaft boss 612 is positioned towards the proximal end of its movement area, near proximal control knob pins 716. When bosses 616 and 612 are in these initial positions, distal tip assembly 104 is generally in the configuration shown in FIG. 3, although distal tip assembly 104 could be previously advanced out of introducer 116. When in a closed configuration, heart valve 304 and valve retainer 302 are encompassed by valve retaining sleeve 204, and valve retaining sleeve 204 is in turn encompassed by introducer 116. In this configuration, the distal end of introducer 116 abuts the proximal end of support arm sleeve 126. Upon introduction into a body channel, distal tip assembly 104 is moved forward while introducer 116 is held at a fixed position, preferably at the apex of the heart after a minithoracotomy procedure, and distal tip assembly 104 is advanced until prosthetic valve 304 reaches a desired implant location, preferably the native valve annulus.

Figure 8:
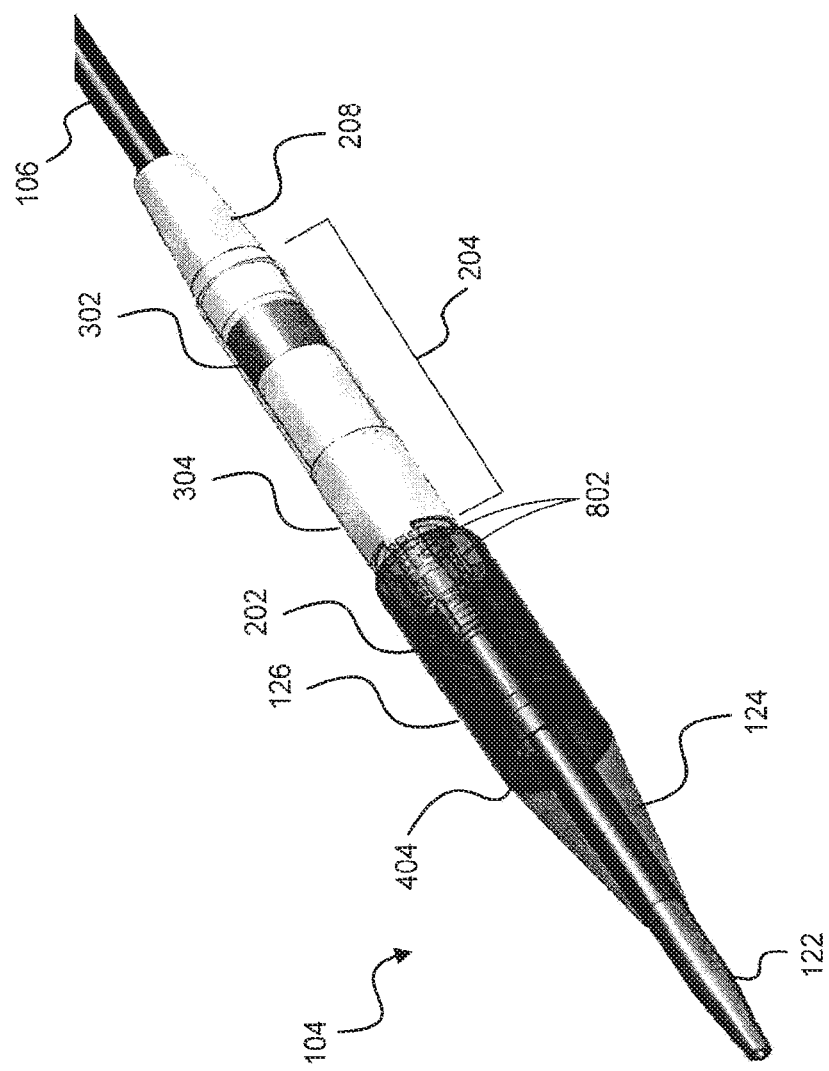
FIG. 8 illustrates the distal tip assembly shown in FIGS. 3 and 4 in one stage of delivery.
Figure 9:
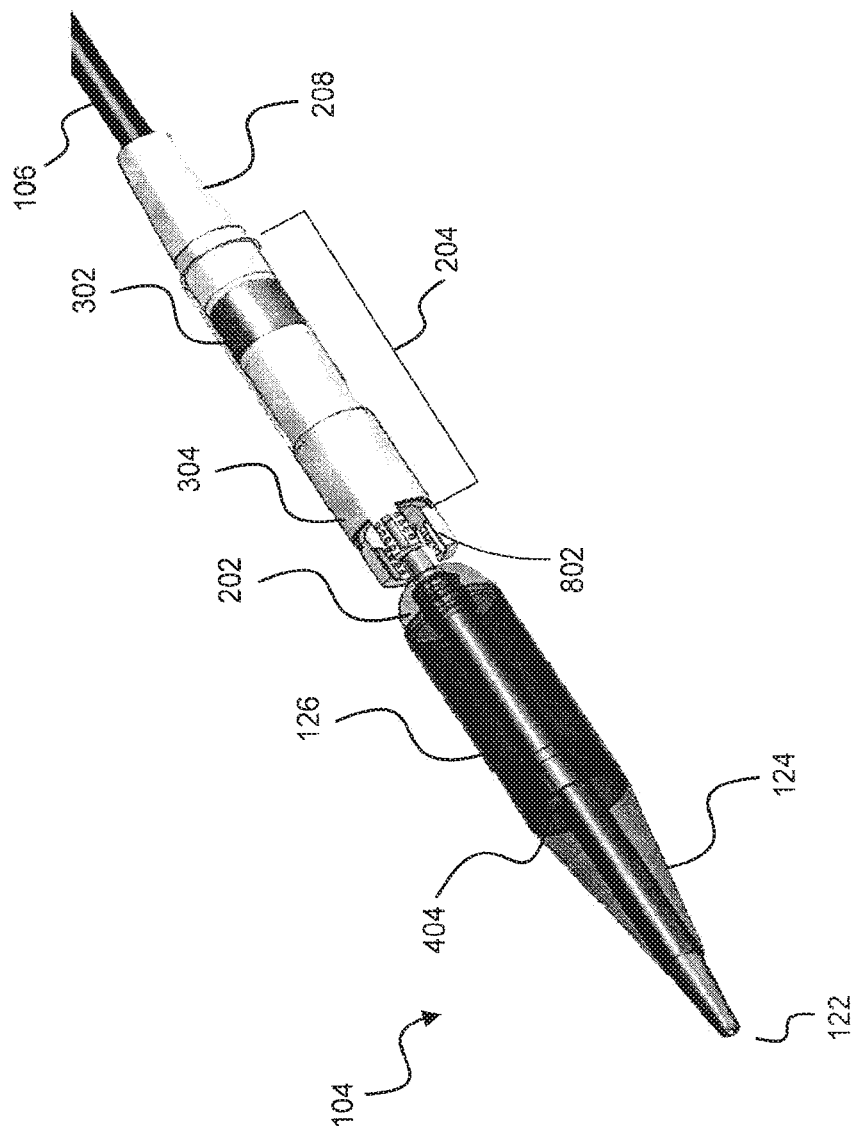
FIG. 9 illustrates the distal tip assembly shown in FIGS. 3 and 4 in a second stage of delivery.
Figure 10:
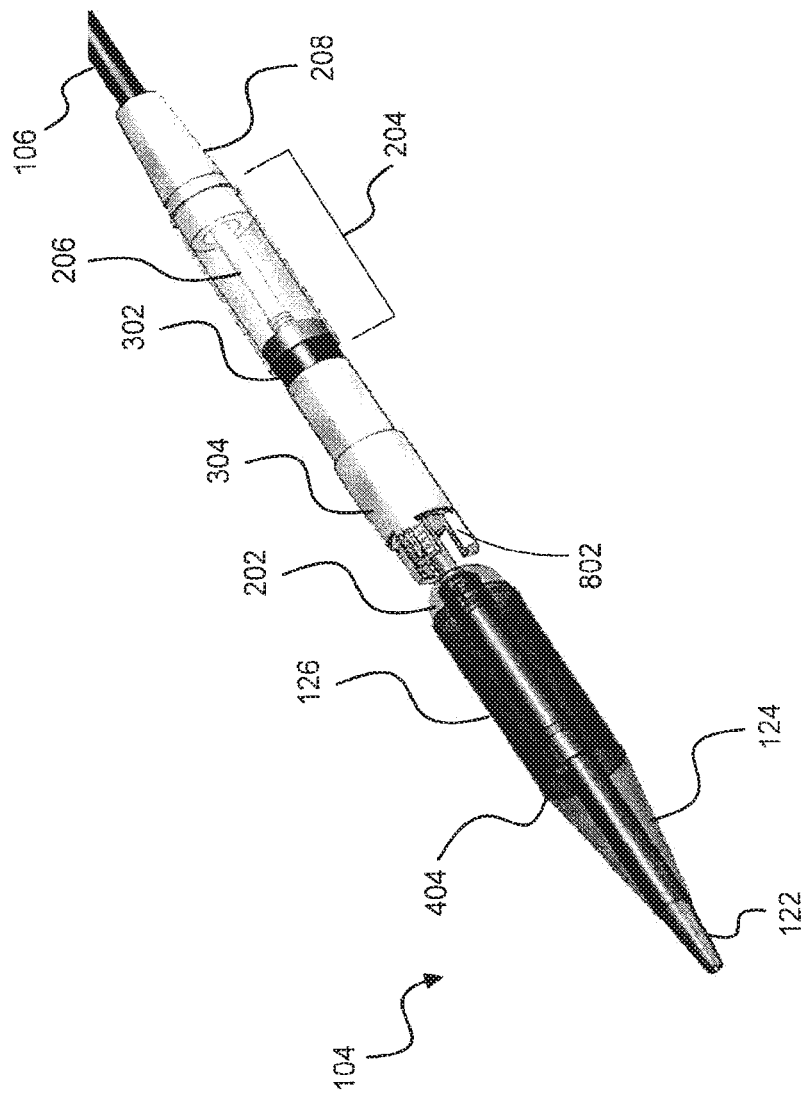
FIG. 10 illustrates the distal tip assembly shown in FIGS. 3 and 4 in a third stage of delivery.

FIG. 8-10 illustrate distal tip assembly 104 in three stages of delivery. In FIG. 8, distal tip assembly has been advanced within the body such that prosthetic valve 304 is positioned and oriented approximately in the native valve location. Distal tip assembly 104 is shown in FIG. 8 in a position that is reached after distal control knob 112 of handle assembly 102 has been rotated in a clockwise direction by a user in order to partially advance distal guide wire shaft boss 616, and thereby guide wire shaft 504, towards the distal end of handle assembly 102. At the stage of delivery shown in FIG. 8, distal guide wire shaft boss 616, and thereby guide wire shaft 504, have not reached their maximum distal position. Advancing guide wire shaft 504 in a distal direction causes connecting fin 404, tip connector 124, and support arm sleeve 126 to advance in a distal direction over slotted tip 122, and away from valve retaining sleeve 204, which remains in its original position because proximal control knob 110 has remained in its original position. Slotted tip 122 is also held stationary during movement of tip connector 124 and support arm sleeve 126 because it is connected to intermediate delivery shaft 206, which is anchored in handle assembly 102. As shown in FIG. 8, valve prosthesis arms 802 are partially exposed, but the support arm sleeve 126 is covering the distal end of arms 802.

To achieve the configuration of distal tip assembly 104 shown in FIG. 9, distal control knob 112 of handle assembly 102 is further rotated in a clockwise direction in order to advance distal guide wire shaft boss 616, and thereby guide wire shaft 504, to their maximum distal location, that is, the location closest to distal control knob pins 714. This distal movement of distal guide wire shaft boss 616 advances connecting fin 404, tip connector 124, and support arm sleeve 126 further distally, fully releasing valve prosthesis arms 802 from support arm sleeve 126. The proximal portion of valve 304, as well as valve retainer 302, remains encompassed by valve retaining sleeve 204. As a further result of advancing support arm sleeve 126 to its furthest distal location, semi-sphere 202 protrudes from the proximal end of support arm sleeve 126.

The clockwise and counterclockwise rotations of distal control knob 112 and proximal control knob 110 described above are merely exemplary. In embodiments of the present invention, the rotation of control knobs 110 and 112 can be reversed, and control knobs 110 and 112 can be rotated in the same direction. Inner threads 602 and 604 can be adjusted accordingly to ensure that guide wire shaft 504 and outer delivery shaft 106 move in the desired axial direction based on the rotational direction of control knobs 110 and 112.

To achieve the configuration of distal tip assembly 104 shown in FIG. 10, proximal control knob 110 of handle assembly 102 is rotated in a counterclockwise direction in order to move outer delivery shaft boss 612 in a proximal direction, thereby withdrawing outer delivery shaft 106, valve retaining sleeve 204, and valve retaining sleeve connector 208 in a proximal direction. As noted above, valve retainer 302 is fixed to intermediate delivery shaft 206, and therefore does not experience axial movement when outer delivery shaft 106 or guide wire shaft 504 are manipulated. In this configuration, valve 304 is fully released from the inside of valve retaining sleeve 204. The distal end of valve retaining sleeve 204 partially covers valve retainer 302. Once released from valve retaining sleeve 204, self-expanding prosthetic valve 304 expands to its open position in the native annulus.

Figure 11:
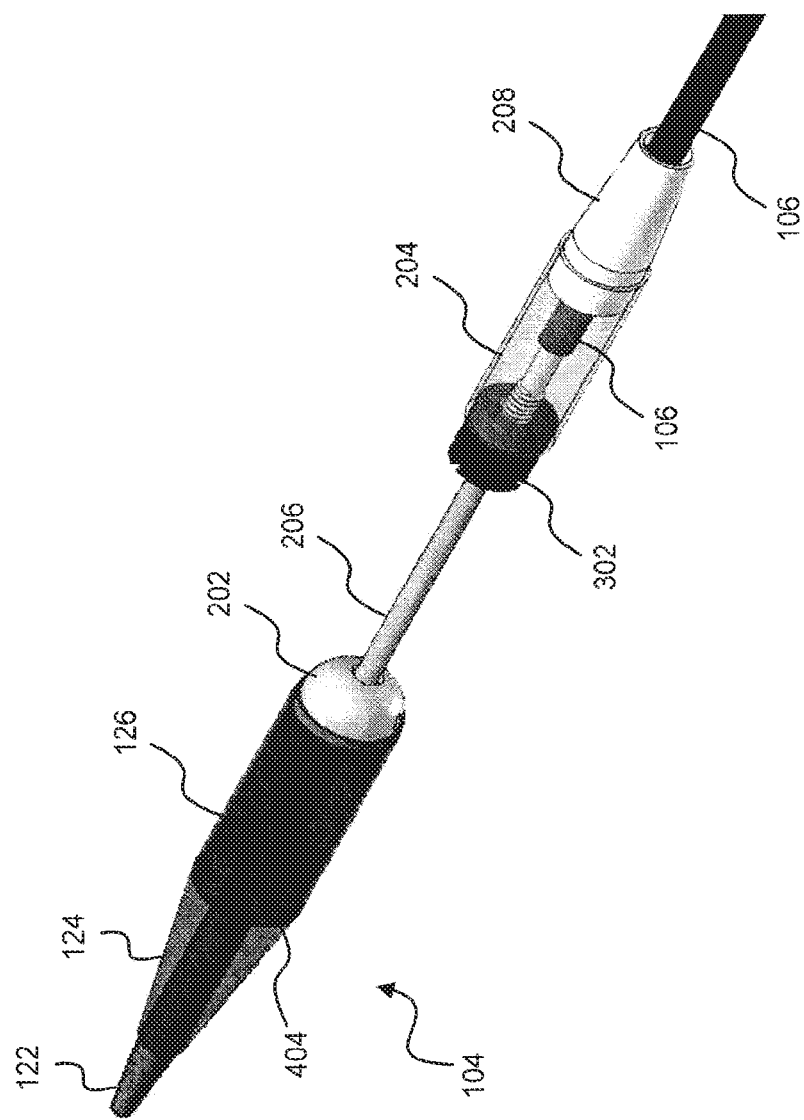
FIG. 11 illustrates the distal tip assembly shown in FIGS. 3 and 4 in one stage of withdrawal.

After valve prosthesis 304 has been delivered to the native annulus, distal tip assembly 104 is prepared for removal from the body. As shown in FIG. 11, distal tip assembly 104 is withdrawn through the expanded valve prosthesis 304. Semi-sphere 202 provides a smooth, non-snagging, surface to aid in withdrawing support arm sleeve through the expanded valve 304 without damaging the valve. Semi-sphere 202 also prevents injuries to body channels as the distal tip assembly 104 is withdrawn from the body. Other structures can be used in place of semi-sphere in embodiments of the present invention. For example, semi-sphere 202 can be replaced with a gently sloping cone or a semi-ellipsoid shape in order to prevent support arm sleeve and other components from snagging on prosthetic valve 304 as the catheter is removed from a patient's body. Semi-sphere 202 can be made from any semi-rigid polymer, metal, or other material suitable for exposure to a patient's circulatory system.

Figure 12:
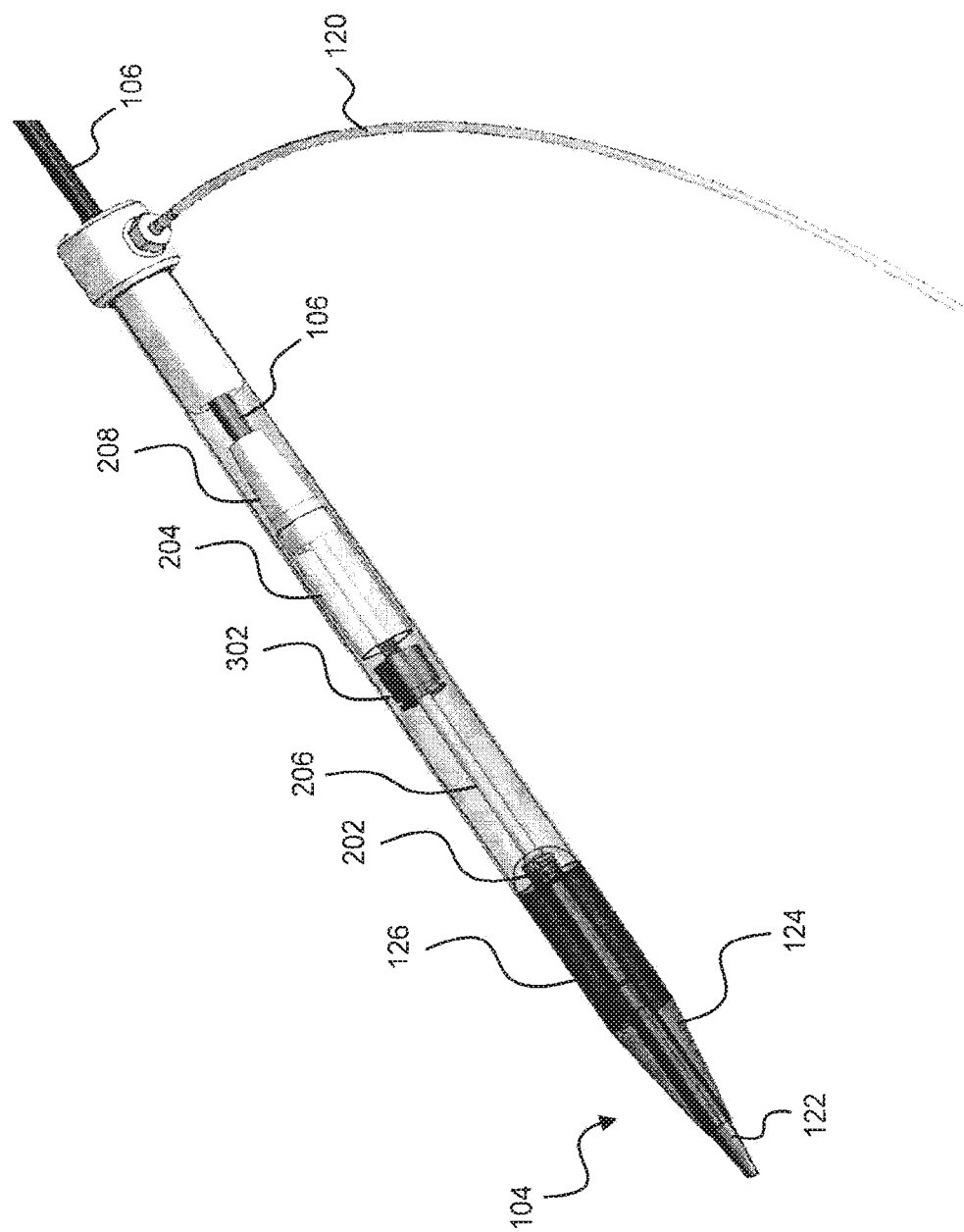
FIG. 12 illustrates the distal tip assembly and introducer shown in FIGS. 3 and 4 in a second stage of withdrawal.

FIG. 12 illustrates the distal tip assembly 104 and introducer 116 shown in FIG. 3 in a second stage of withdrawal. In this stage, distal tip assembly 104 has been withdrawn to the apex of the heart. Semi-sphere 202, valve retainer 302, valve retaining sleeve 204, and valve retaining sleeve connector 208 are encompassed by introducer 116. The distal end of introducer 116 mates with semi-sphere 202 and abuts the proximal end of support arm sleeve 126. Introducer 116 and distal tip assembly 104 are then removed from the body.

Figure 13:
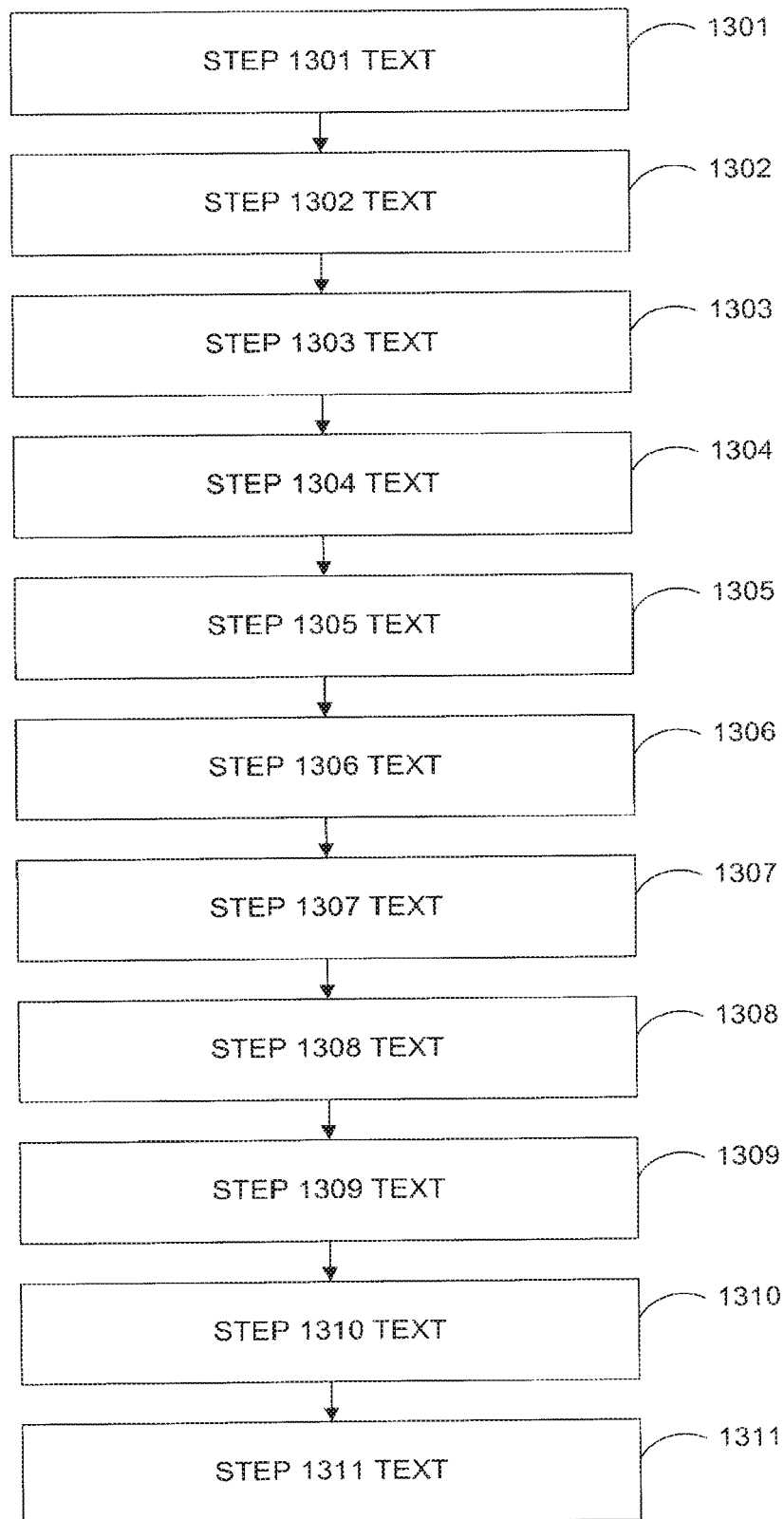
FIG. 13 is a flow diagram that is used as an aid to describe a method of implanting a prosthetic heart valve in a patient.

A method of implanting a heart valve via a transapical approach using a catheter according to one embodiment of the present invention will be described with reference to FIG. 13. First, in step 1301, a patient's chest and heart apex are prepped for an implantation procedure, preferably by minithoracotomy or a similar procedure. Various preparation procedures that provide access to the heart can also be used in embodiments of the present invention. For example, hemistemotomy or sternotomy can be used to gain access to the heart, although these procedures are less desirable because they are more invasive than minithoracotomy and can result in extended post-operative recovery times. In step 1302, the user de-airs the catheter assembly 100 and places the catheter assembly 100 over a guide wire and advances the distal tip assembly 104 through the minithoracotomy and to the apex of the heart. Slotted tip 122 penetrates the apex of the heart to allow access to the interior of the heart. In step 1303, the user positions introducer 116 across the apex of the heart, and advances the distal tip assembly 104 distally while holding the introducer stationary. In step 1304, distal tip assembly 104 is advanced until the prosthetic valve 304 is correctly positioned and oriented in the native valvular annulus.

Steps 1305 through 1307 release the prosthetic valve 304 from the distal tip assembly 104. In step 1305, the user rotates distal control knob 602 to move the support arm sleeve 126 distally to release the proximal end of valve prosthesis arms 802. Note that the distal portion of valve prosthesis arms 802 are still contained within support arm sleeve 126, which allows the user to retract the arms 802 if the prosthetic valve 304 is not correctly positioned. If the user is satisfied that prosthetic valve 304 is properly positioned and oriented, the user further rotates the distal control knob 602 (step 1306) to advance support arm sleeve 126 further distally. This fully releases the valve prosthesis arms 802 from support arm sleeve 126. Then, in step 1307, the user retracts the valve retaining sleeve 204 by rotating the proximal control knob 110, allowing the prosthetic valve 304 to fully expand in the native annulus.

In steps 1308-1310, the distal tip assembly 104 and introducer 116 are removed from the body. First, in step 1308, semi-sphere 202, support arm sleeve 126, tip connector 124, and slotted tip 122 are pulled back through the valve 304. Semi-sphere 202 prevents the support arm sleeve 126 from snagging on and damaging valve 304. In step 1309, distal tip assembly 104 is withdrawn into introducer 116, which encloses the device. The introducer 116 and distal tip assembly 104 are then withdrawn from the heart and from the body (step 1310). The body can then be closed up in the conventional fashion (step 1311).

Although the method described with reference to FIG. 13 has been described with reference to a transapical approach, components and methods according to embodiments of the present invention can be used in conjunctions with catheters designed for alternate approaches. For example, distal tip assembly 104 and/or handle assembly 102, or components thereof, can be used in catheters designed for delivery of a heart valve via a transfemoral approach.

Figure 14:
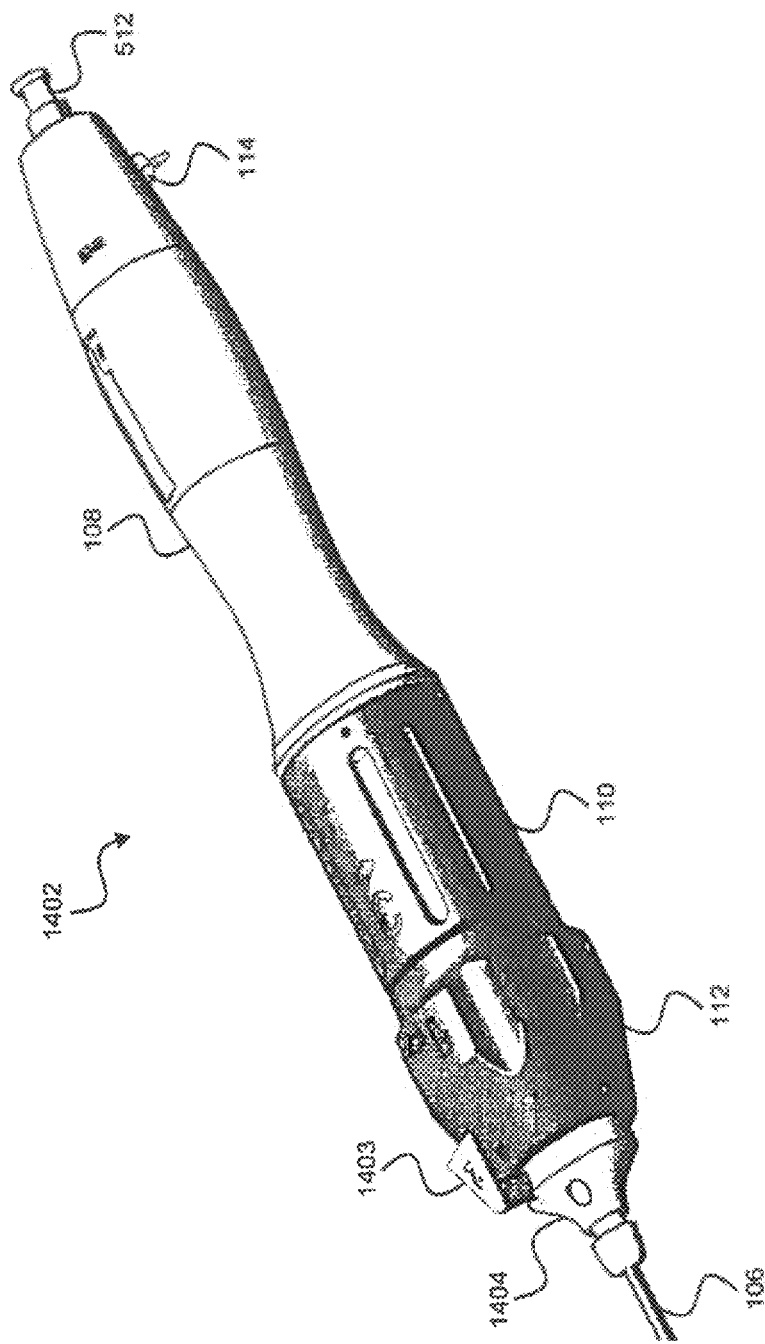
FIG. 14 illustrates a delivery catheter handle in accordance with one embodiment presented herein, including one embodiment of a support arm release button.
Figure 15:
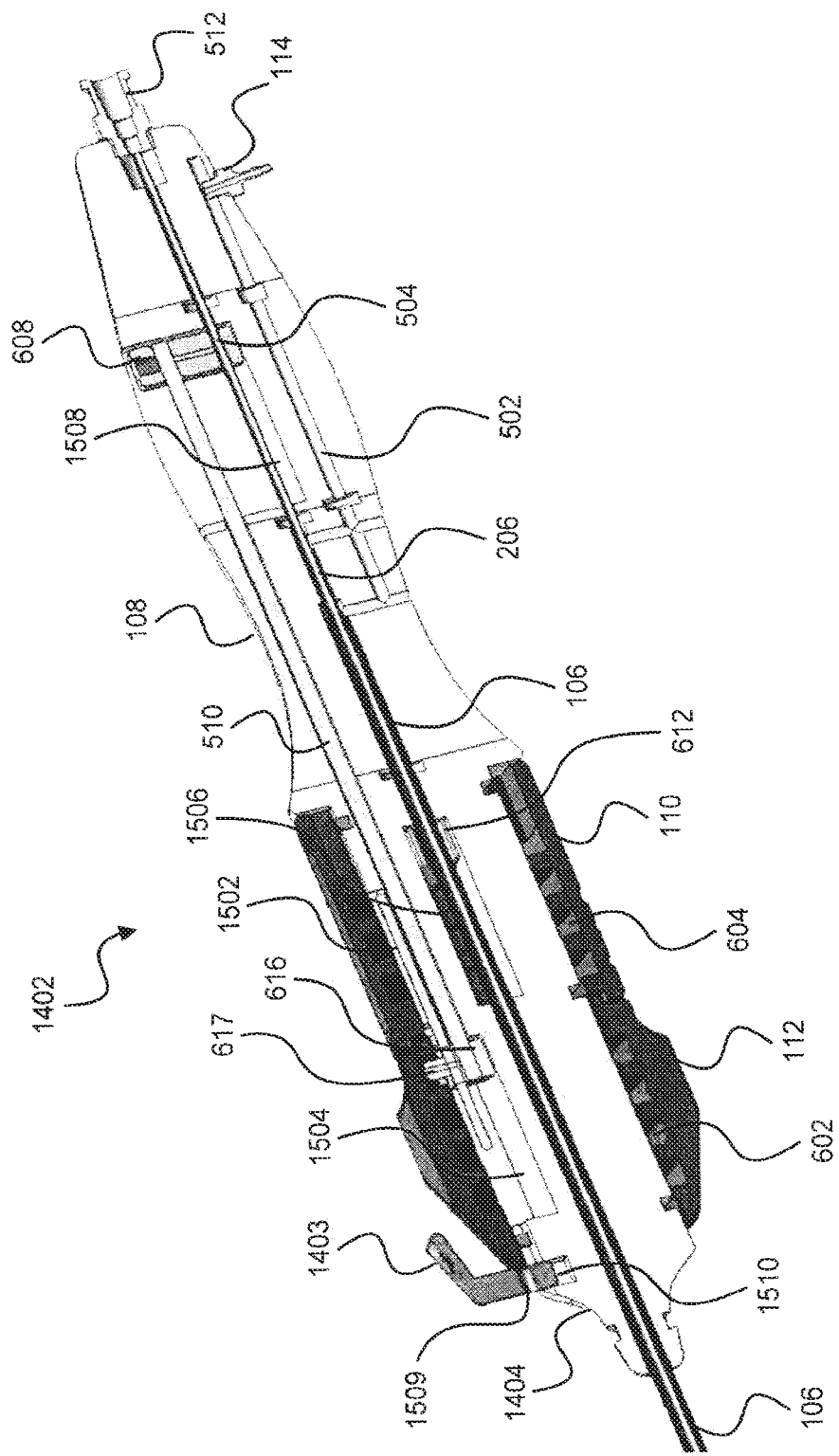
FIG. 15 is a cross-sectional view of a delivery catheter handle in accordance with the embodiment illustrated in FIG. 14.

FIG. 14 illustrates a delivery catheter handle assembly 1402 according to another embodiment of the present invention including a support arm release button 1403, also referred to herein as a safety button, that provides for increased accuracy in positioning and deploying a prosthetic heart valve at a desired location in the body. The construction and configuration of handle assembly 1402 is similar in many respects to that of handle assembly 102, and similar components are referred to herein using the same reference numbers used to describe the components of handle assembly 102. Handle assembly 1402 includes a main handle 108, a proximal control knob 110, and a distal control knob 112. The handle sections of handle assembly 1402 are preferably connected using O-rings (not shown), but other connection mechanisms are possible. A guide wire port 512 and a flushing port 114 are also provided, as shown in FIG. 15. Outer delivery shaft 106 extends from the distal tip of handle assembly 1402. Handle assembly 1402 further includes a support arm release button 1403 positioned on the distal tip 1404 of handle assembly 1402.

FIG. 15 is a cross-sectional view of handle assembly 1402. Handle assembly 1402 includes a distal guide wire shaft boss 616 configured to engage the inner threads 602 of the distal control knob 112. Distal guide wire shaft boss 616 is slidably located in a channel 1504, allowing axial movement of the distal guide wire shaft boss 616. Distal guide wire shaft boss 616 preferably has a tongue 617 that engages inner threads 602 of distal control knob 112. Inner threads 602 are formed such that, as distal control knob 112 is rotated in a clockwise direction by a user, distal guide wire shaft boss 616 is forced in a distal direction within channel 1504, that is, towards the distal end of handle assembly 1402 and the distal end of channel 1504. Distal guide wire shaft boss 616 is connected to proximal guide wire shaft boss 608 by connecting bar 510. Proximal guide wire shaft boss 608 is slidably located in a channel 1508, allowing axial movement of the proximal guide wire shaft boss 608. Proximal guide wire shaft boss 608 is connected to guide wire shaft 504. Therefore, in operation, clockwise rotation of distal control knob 112 moves distal guide wire shaft boss 616 towards the distal end of channel 1504. Because distal guide wire shaft boss 616 is coupled to guide wire shaft 504 through connecting bar 510 and proximal guide wire shaft boss 608, guide wire shaft 504 moves in a distal direction when distal guide wire shaft boss 616 moves in a distal direction. Although a specific manner of connecting distal guide wire shaft boss 616 to guide wire shaft 504 is described above, it is understood that in other embodiments of the present invention alternate mechanisms can be used to ensure that rotation of distal control knob 112 results in axial movement of guide wire shaft 504.

Handle assembly 1402 further includes an outer delivery shaft boss 612 configured to engage the inner threads 604 of the proximal control knob 110. Outer delivery shaft boss 612 is slidably located in a channel 1506 allowing axial movement of the outer delivery shaft boss 612. Specifically, outer delivery shaft boss 612 preferably has a tongue 618 (shown in FIG. 16A) that engages inner threads 604 of proximal control knob 110. Outer delivery shaft boss 612 is connected to outer delivery shaft 106. In operation, counter-clockwise rotation of proximal control knob 110 moves outer delivery shaft boss 612 towards the proximal end of channel 1506. Because outer delivery shaft boss 612 is coupled to outer delivery shaft 106, outer delivery shaft 106 moves in a proximal direction when proximal control knob 110 moves in a proximal direction. Although a specific manner of connecting outer delivery shaft boss 612 to outer delivery shaft 106 is described above, it is understood that in other embodiments of the present invention, alternate mechanisms can be used to ensure that rotation of outer delivery shaft boss 612 results in axial movement of outer delivery shaft 106.

Handle assembly 1402 also includes an intermediate delivery shaft 206. Intermediate delivery shaft 206 is fixedly secured to the inside of main handle 108, preferably by an O-ring. It is understood that intermediate delivery shaft 206 can be secured to main handle 108 by other methods, for example, by welding, bolting, over-molding, etc. Guide wire shaft 504 is encompassed by, but not affixed to, intermediate delivery shaft 206 such that guide wire shaft 504 is axially movable with respect to intermediate delivery shaft 206. Intermediate delivery shaft 206 is encompassed by, but not affixed to, outer delivery shaft 106 such that outer delivery shaft 106 is axially movable with respect to intermediate delivery shaft 206. The entire catheter assembly 100 can be placed over a pre-positioned guide wire (not shown) by sliding guide wire shaft 504 over the guide wire and sliding the guide wire out of guide wire port 512. Guide wire port 512 can also be used as a supplemental flushing port. Handle assembly 1402 further includes a flushing channel 502 located within main handle 108. Flushing channel 502 is fluidly connected to the space between outer delivery shaft 106 and intermediate delivery shaft 206 and the space between intermediate delivery shaft 206 and guide wire shaft 504. Flushing channel 502 is fluidly connected to flushing port 114. In some embodiments, flushing channel 502 is fluidly connected to guide wire port 512 in addition to, or instead of, flushing port 114.

Handle assembly 1402 further includes a support arm release button 1403 located on a distal tip section 1404. Support arm release button 1403 is located in a radial channel 1510, allowing radial movement thereof. Preferably, support arm release button 1403 is spring loaded and is pre-biased in the upward position shown in FIG. 15. A locking pin 1502 is coupled, or formed integrally with, distal guide wire shaft boss 616. As will be described in further detail with reference to FIG. 17B, support arm release button 1403 includes a channel 1509 configured to receive the distal portion of locking pin 1502. As shown in FIG. 15, when button 1403 is in its upwardly pre-biased position, channel 1509 is not aligned with the distal portion of locking pin 1502. Thus, distal guide wire shaft boss 616 and locking pin 1502 are prevented from advancing to their full distal position in channel 1504 because the distal portion of locking pin 1502 is blocked from advancing fully by the bottom portion of button 1403, as shown in FIG. 17B. When downward pressure is applied to button 1403, the button 1403 and channel 1509 are forced downward within channel 1510. When the button 1403 is fully depressed, channel 1509 is generally aligned with the locking pin 1502. The distal tip of locking pin 1502 can then pass into channel 1509, allowing the distal guide wire shaft boss 616 to be advanced fully distally in channel 1504. Some benefits of such a configuration are detailed with respect to FIGS. 17 and 18.

The size and shape of the support arm release button shown in FIG. 15 is merely exemplary. It is understood that many button sizes and shapes can be used. Button 1403 can be pre-biased in the upward configuration using a variety of mechanisms other than spring loading. For example, button 1403 can be provided with a tongue, which can be spring loaded, and handle assembly 1402 can be provided with grooves to receive the tongue corresponding to an upward position and a downward position of the button. After use, the button can be reset by a user to its upward position. In addition, other mechanisms can be used to place a channel in alignment with locking pin 1502. For example, a sliding tab having an angled bottom surface can be used in place of button 1403. Depending on the orientation of the angled bottom surface, advancing the tab distally, proximally, or left or right on the handle can force a spring-loaded button underneath the sliding tab downward in order to align a channel in the button with the locking pin 1502. Alternately, a lever having a channel therein can be used in place of button 1403. In an initial position, the level can be positioned such that the channel is not aligned with locking pin 1502. By forcing the lever to either the right or left, depending on the location of the channel on the lever body, the channel can be aligned with the locking pin 1502.

Figures 16A, 16B:
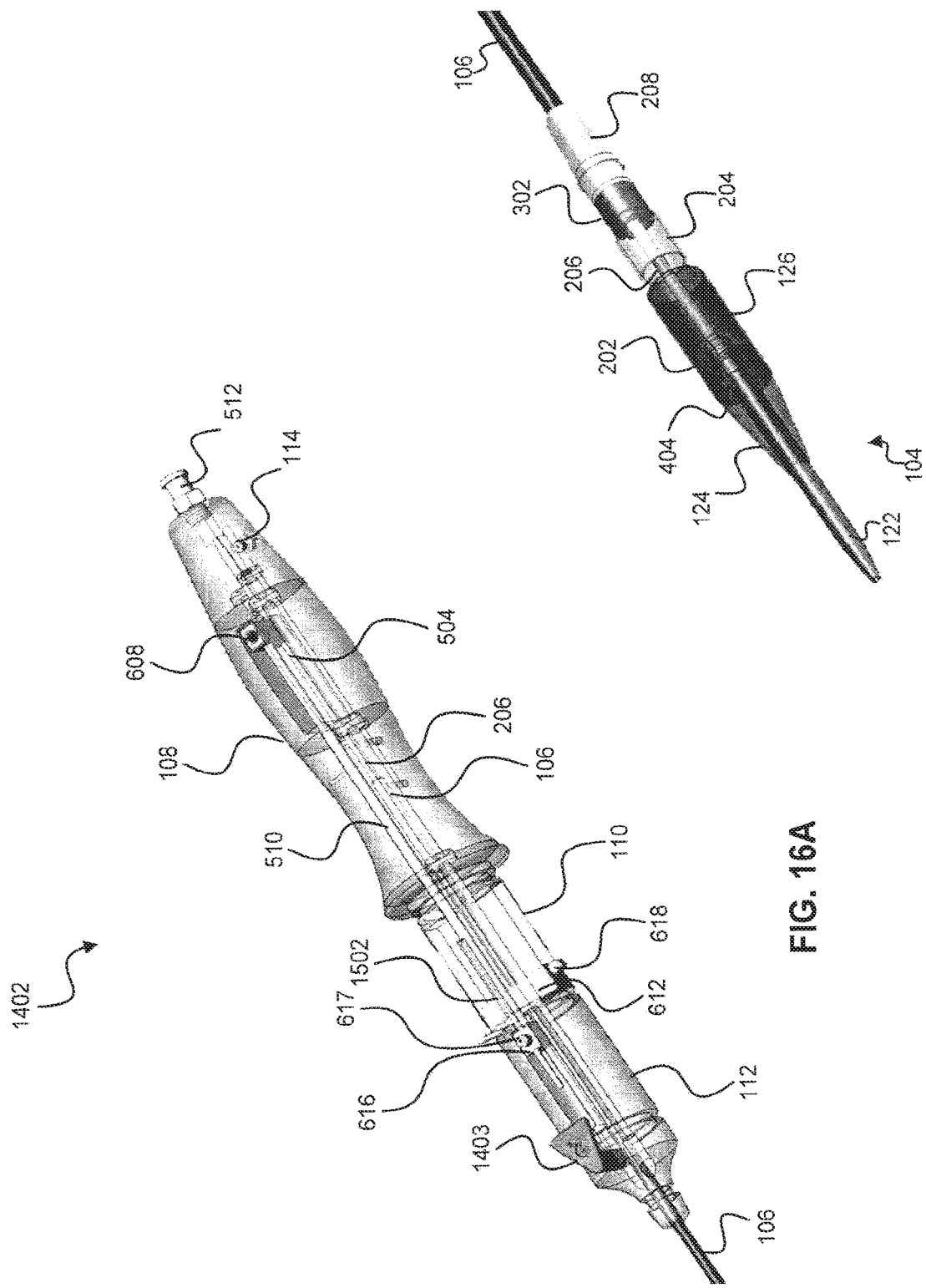
FIGS. 16A and 16B illustrate a delivery catheter handle and distal tip assembly of a delivery catheter according to one embodiment of the present invention at one stage of delivery.

FIG. 16A illustrates the interior of handle assembly 1402 at a first delivery stage. FIG. 16B illustrates the configuration of distal tip assembly 104 corresponding to the handle configuration shown in FIG. 16A. Distal tip assembly 104 has been described in detail above with reference to FIGS. 4 and 8-12. At the beginning of a procedure, distal guide wire shaft boss 616 is positioned towards the proximal end of channel 1504, and outer delivery shaft boss 612 is positioned towards the distal end of channel 1506. When bosses 616 and 612 are in these positions, distal tip assembly 104 is generally in the configuration shown in FIG. 16B. When in a closed configuration, heart valve 304 (not shown in FIG. 16B) and valve retainer 302 are encompassed by valve retaining sleeve 204. Distal tip assembly 104 is moved forward while introducer 116 is held at a fixed position, preferably at the apex of the heart after a minithoracotomy procedure, and distal tip assembly 104 is advanced until prosthetic valve 304 reaches a desired implant location, preferably the native valve annulus.

After the distal tip assembly has reached the desired implant location area, a user rotates distal control knob 112 in a clockwise direction in order to partially advance distal guide wire shaft boss 616, and thereby guide wire shaft 504, towards the distal end of channel 1504. This configuration is shown in FIGS. 17A and 17B. Because support arm release button 1403 is still in the pre-biased upward position, the distal guide wire shaft boss 616 cannot move past the point at which locking pin 1502 abuts the button 1403, as shown in more detail in FIG. 17B. Thus, distal guide wire shaft boss 616, and thereby guide wire shaft 504, have not reached their maximum distal position. Advancing guide wire shaft 504 distally to this point causes connecting fin 404, tip connector 124, and support arm sleeve 126 to advance in a distal direction over slotted tip 122, and away from valve retaining sleeve 204, which remains in its original position because proximal control knob 110 has remained in its original position. Slotted tip 122 is also held stationary during movement of tip connector 124 and support arm sleeve 126 because it is connected to intermediate delivery shaft 206, which is anchored in handle assembly 1402. As shown in FIG. 17C, valve arms 802 are partially exposed, but the support arm sleeve 126 is covering the distal end of arms 802. Thus, the inclusion of support arm release button 1403 and locking pin 1502 decreases the incidence of operator error because a user can precisely advance the support arm sleeve 126 to the position where the valve arms 802 are partially, but not completely, removed from support arm sleeve 126. Specifically, when distal guide wire shaft boss 616 has been advanced to the point where locking pin 1502 is abutting button 1403, further rotation of distal control lamb 112 in a clockwise direction is prevented.

Figures 18A, 18B:
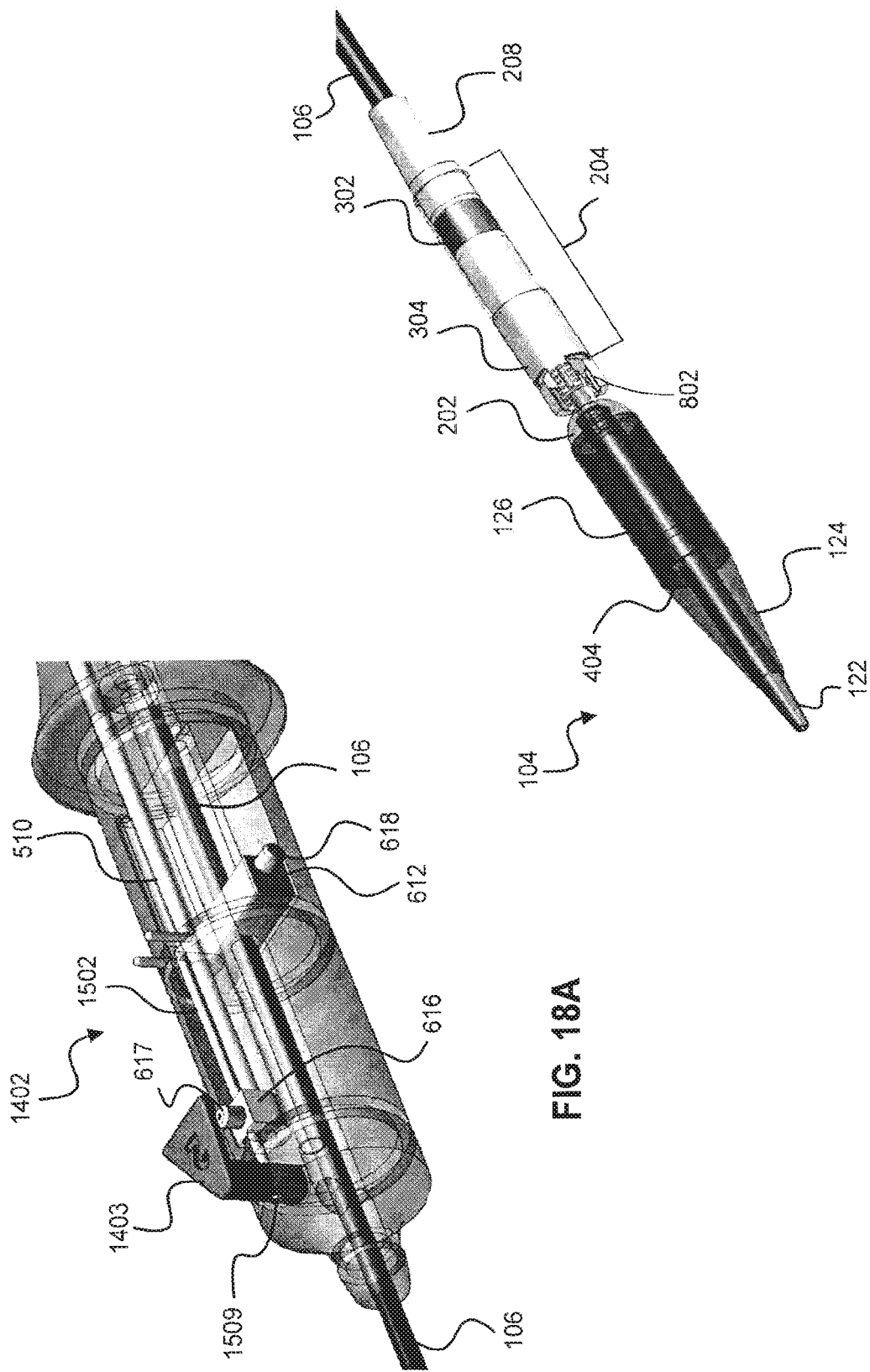
FIGS. 18A and 18B illustrate a delivery catheter handle and distal tip assembly of a delivery catheter according to one embodiment of the present invention at a third stage of delivery.
Figure 20:
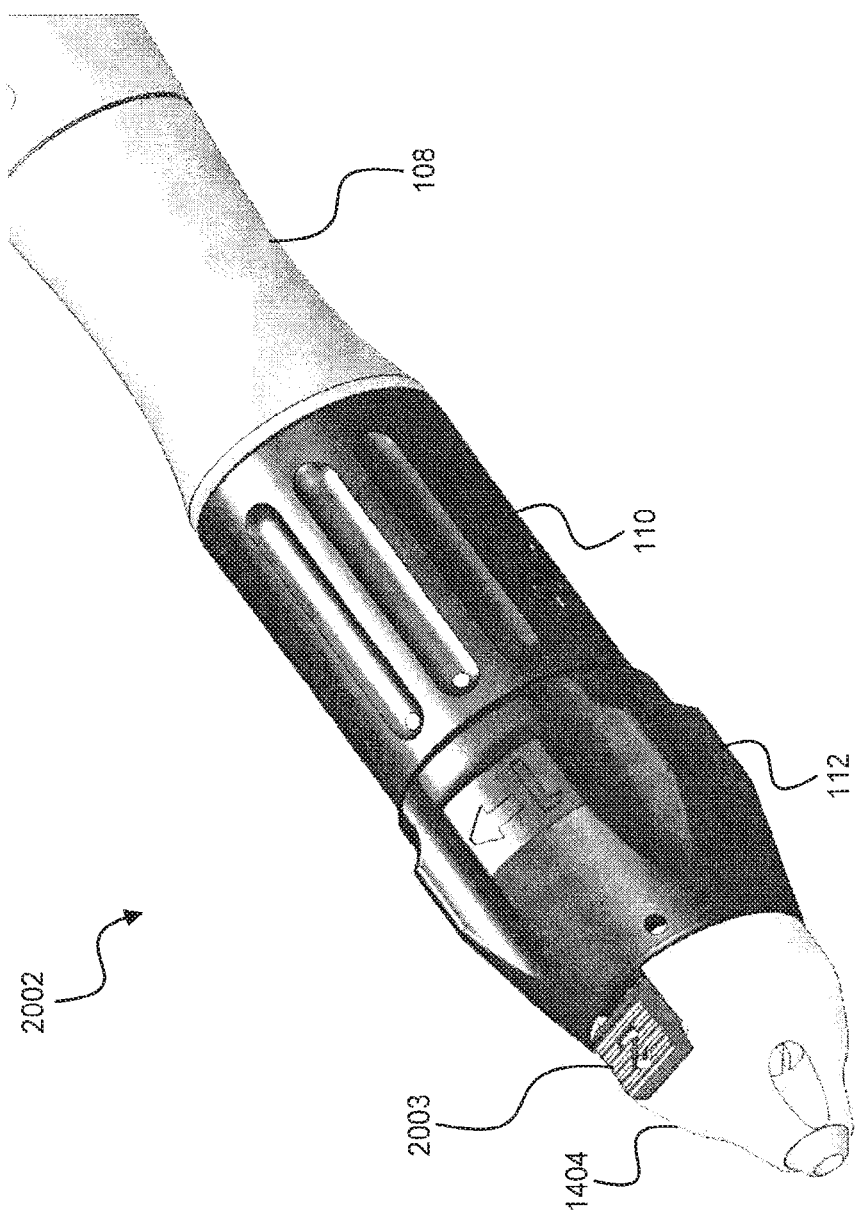
FIG. 20 illustrates a delivery catheter handle according to one embodiment presented, including an alternate support arm release button configuration.

To achieve the configuration of distal tip assembly 104 shown in FIG. 18B, button 1403 is moved to its downward position in order to align channel 1509 with the distal end of locking pin 1502. Distal control knob 112 is then further rotated in a clockwise direction in order to advance the distal end of locking pin 1502 into channel 1509. Rotation continues until distal guide wire shaft boss 616 reaches the distal end of channel 1504, as shown in FIG. 18A. When this position is reached, further rotation of distal control knob 112 is prevented. This distal movement of distal guide wire shaft boss 616, and thereby guide wire shaft 504, advances connecting fin 404, tip connector 124, and support arm sleeve 126 further distally, fully releasing valve prosthesis arms 802 from support arm sleeve 126. The proximal portion of valve 304, as well as valve retainer 302, remains encompassed by valve retaining sleeve 204. As a further result of advancing support arm sleeve 126 to its furthest distal location, semi-sphere 202 protrudes from the proximal end of support arm sleeve 126.

As with handle assembly 102, the clockwise and counterclockwise rotations of distal control knob 112 and proximal control knob 110 on handle assembly 1402 are merely exemplary. In embodiments of the present invention, the rotation of control knobs 110 and 112 can be reversed, and control knobs 110 and 112 can be rotated in the same direction. Inner threads 602 and 604 can be adjusted accordingly to ensure that guide wire shaft 504 and outer delivery shaft 106 move in the desired axial directions based on the rotational direction of control knobs 110 and 112.

To achieve the configuration of distal tip assembly 104 shown in FIG. 19B, proximal control knob 110 of handle assembly 1402 is rotated in a counterclockwise direction in order to move outer delivery shaft boss 612 in a proximal direction, thereby withdrawing outer delivery shaft 106, valve retaining sleeve 204, and valve retaining sleeve connector 208 in a proximal direction. Valve retainer 302 is fixed to intermediate delivery shaft 206, and therefore does not experience axial movement when outer delivery shaft 106 or guide wire shaft 504 are manipulated. In this configuration, valve 304 is fully released from the inside of valve retaining sleeve 204. The distal end of valve retaining sleeve 204 partially covers valve retainer 302. Once released from valve retaining sleeve 204, self-expanding prosthetic valve 304 expands to its open position in the native annulus.

After valve prosthesis 304 has been delivered to the native annulus, the catheter assembly is withdrawn from the body in the manner described above with reference to FIGS. 11 and 12.

Figure 21:
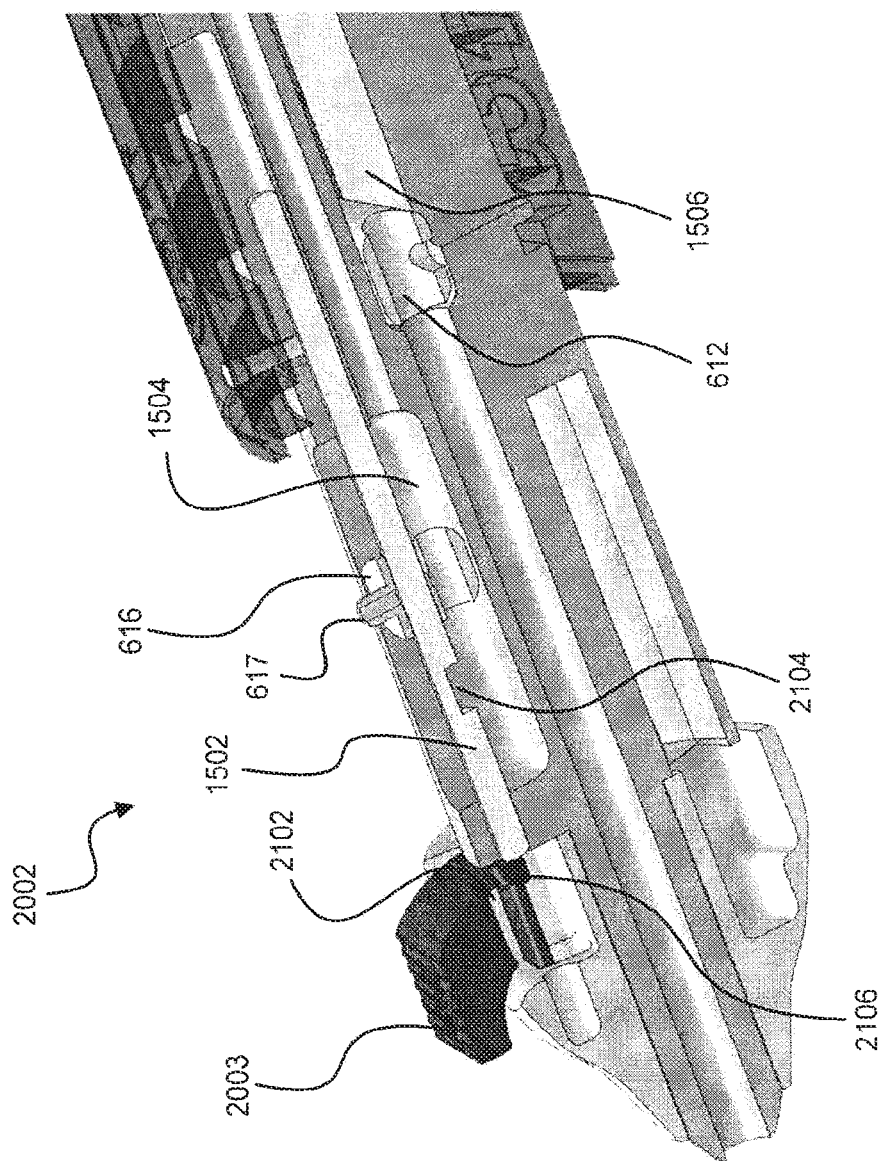
FIG. 21 is a cross-sectional view of the delivery catheter handle illustrated in FIG. 20, illustrating the support arm release button in one stage of operation.

FIGS. 20-23 illustrate a catheter handle assembly 2002 according to one embodiment of the present invention. Handle assembly 2002 is generally constructed and operated in the manner described above with reference to handle assembly 1402 in FIGS. 14-19B. However, handle assembly 2002 features an alternative embodiment of a support arm release button 2003 according to another embodiment of the present invention. Support arm release button 2003 is preferably spring loaded and biased in the upward position shown in FIG. 21, but other attachment and operation methods can be used, as described above with reference to handle assembly 1402. As shown in FIG. 21 support arm release button 2003 is formed with a channel 2102 therein. At the proximal end of channel 2102, a locking tab 2002 is formed, which extends upward from the bottom surface of channel 2102. A corresponding notch 2104 is formed in locking pin 1502, which is attached to distal guide wire shaft 616 as described above. As pictured in FIG. 21, distal control knob 112 has been rotated in a clockwise direction to move distal guide wire shaft boss 616 distally within channel 1504. The distal tip of locking pin 1502 abuts the bottom portion of button 2003, thereby preventing further rotation of distal control knob 112 and signaling a user that the distal tip assembly 104 has reached the position shown in FIG. 17C.

Figure 22:
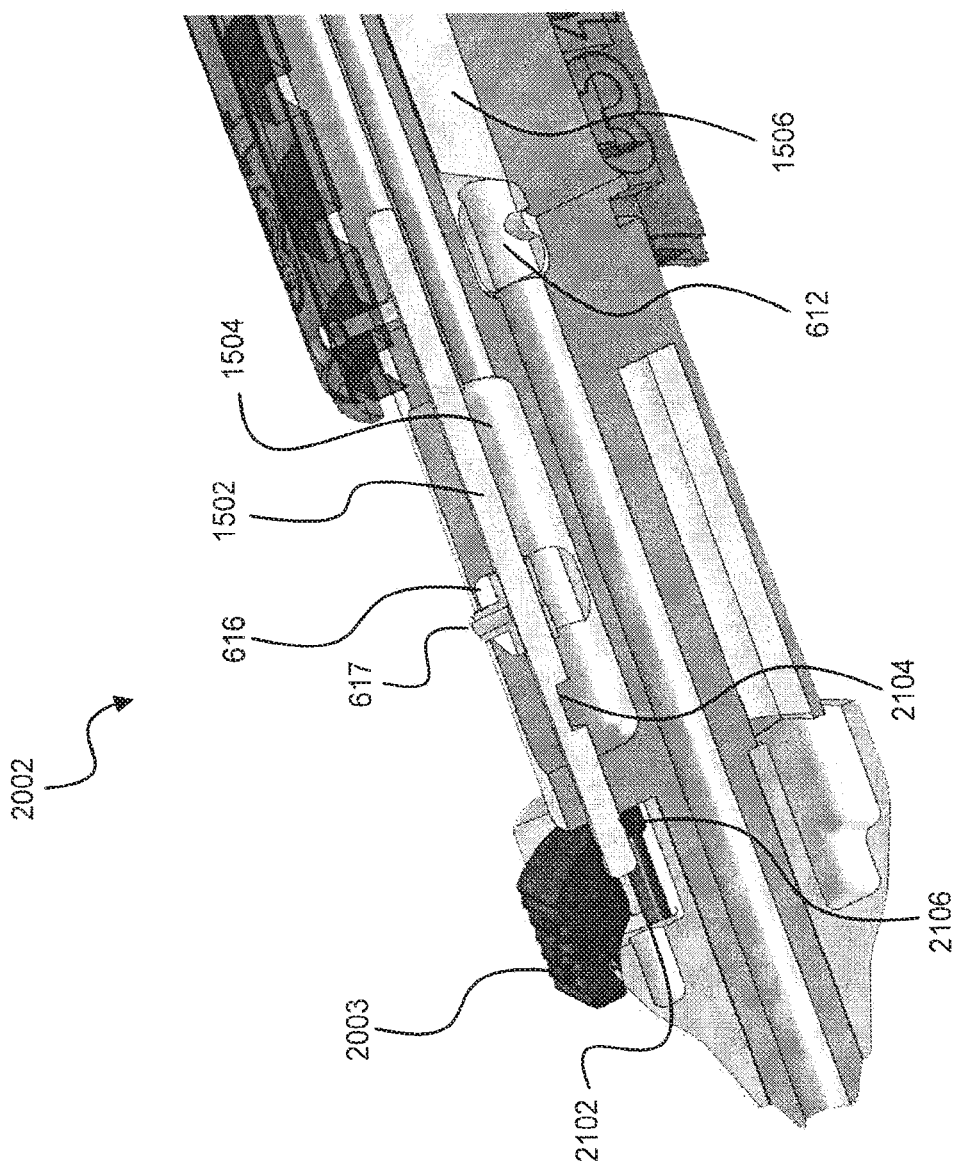
FIG. 22 is a cross-sectional view of the delivery catheter handle illustrated in FIG. 20, illustrating the support arm release button in another stage of operation.
Figure 23:
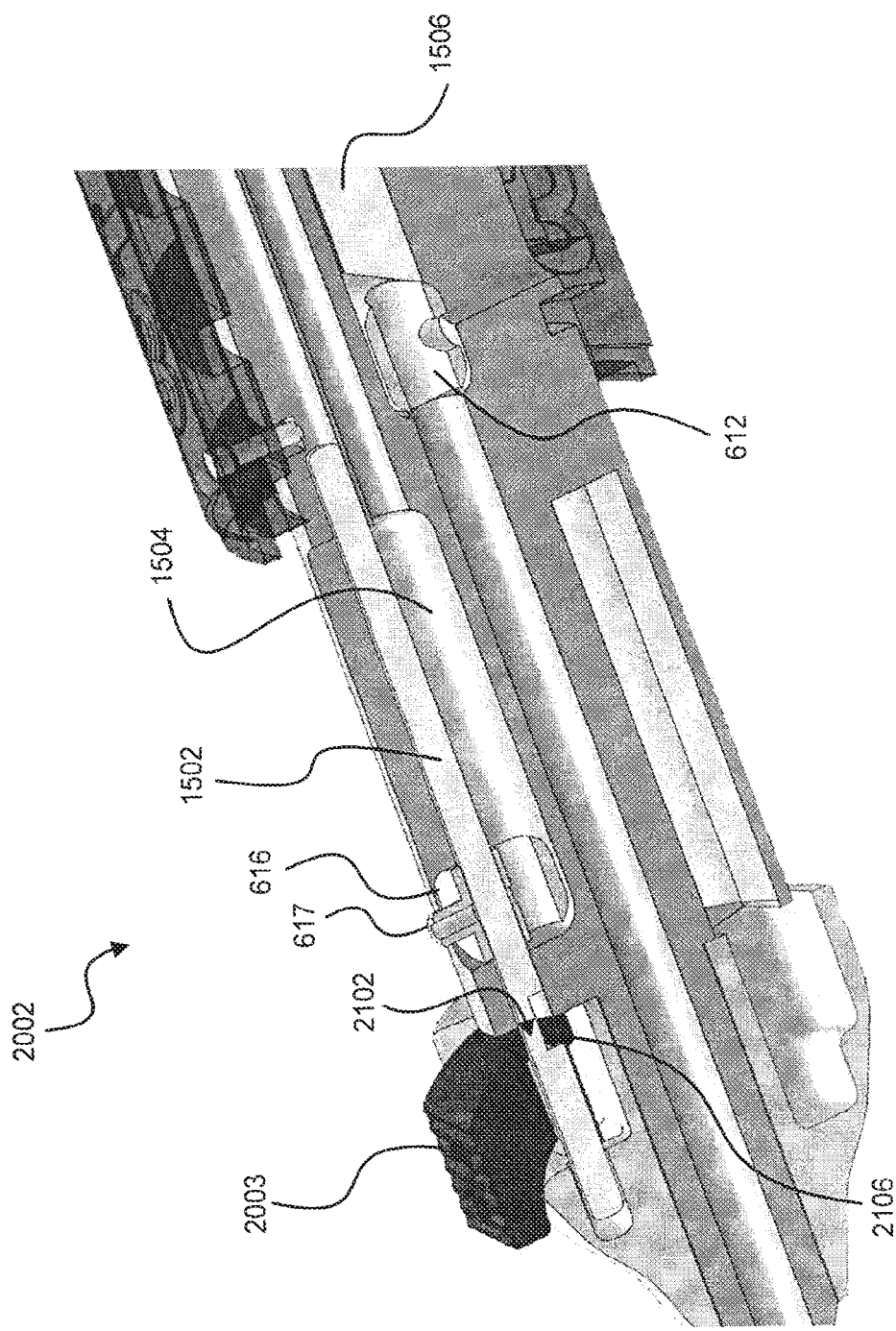
FIG. 23 is a cross-sectional view of the delivery catheter handle illustrated in FIG. 20, illustrating the support arm release button in yet another stage of operation.

As shown in FIG. 22, support arm release button 2003 is then pressed and thereby moved to its downward position, aligning channel 2102 with the distal tip of locking pin 1502. The distal tip of locking pin 1502 is then able to enter channel 2102, and distal control knob 112 can be rotated to bring distal guide wire shaft boss 616 to its most distal position in channel 1504, as shown in FIG. 23. At this point, distal tip assembly 104 of the catheter is in the position shown in FIG. 18B. When guide wire shaft boss 616 is in its most distal position, locking tab 2106 is aligned with notch 2104 in locking pin 1502. Support arm release button 2003 rises slightly due to its spring-loaded upward bias, thereby locking the locking pin 1502 in position because tab 2106 is mated with notch 2106. This locking action prevents unintentional rotation of distal control knob 112 during an implantation procedure, thereby ensuring that support arm sleeve 126 remains in its most distal orientation, shown in FIG. 18B, as the remainder of the procedure is performed.

Handle assemblies 1402 and 2002 can be substituted for handle assembly 102 in catheter 100. Heart valves can be implanted in a patient utilizing handle assembly 1402 or handle assembly 2002 in conjunction with catheter 100 in generally the same manner as described with reference to FIG. 13, with the following modifications to steps 1305 and 1306. In step 1305, when using handle assembly 1402 or 2002, the user rotates distal control knob 612 to move the support arm sleeve 126 distally to release the proximal end of valve prosthesis arms 802 until the distal end of locking pin 1502 abuts the support arm release button 1403 or 2003. The distal portion of valve prosthesis arms 802 are still contained within support arm sleeve 126 at this point, which allows the user to reposition the prosthetic valve 304 if the valve arms 802 are not correctly positioned. If the user is satisfied that prosthetic valve 304 is properly positioned and oriented, the user applies downward pressure to support arm release button 1403 or 2003 in order to align channel 1509 or 2102 with the distal end of locking pin 1502, and further rotates the distal control knob 612 to advance support arm sleeve 126 to its maximum distal position relative to slotted tip 122 (step 1306). With respect to handle assembly 2002, this action locks the distal control knob 112, preventing further rotation thereof in any direction. This fully releases the valve prosthesis arms 802 from support arm sleeve 126. Operation of proximal control knob 110 and withdrawal of the catheter assembly from the body can then proceed as detailed in steps 1307-1311.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

EXAMPLES

The following paragraphs serve as examples of the above-described embodiments.

Example 1

One embodiment provides a catheter for delivering an expandable prosthesis, the catheter having a proximal end and a distal end. The catheter includes a handle assembly on the proximal end of the catheter. The handle assembly includes a rotatable distal control knob and a rotatable proximal control knob. A distal tip assembly including a first sleeve and a second sleeve is provided on the distal end of the catheter. The catheter has a first elongate member extending from the handle assembly. The first elongate member has a proximal end and a distal end and the first sleeve is connected to the distal end of the first elongate member. The catheter also has a second elongate member extending from the handle assembly. The second elongate member has a proximal end and a distal end and the second sleeve is connected to the distal end of the second elongate member. A safety button is provided on the handle assembly. The rotatable distal control knob is movably connected to the first elongate member, and the catheter is configured such that rotation of the rotatable distal control knob advances the first sleeve in a distal direction. The safety button is configured to lock the rotatable distal control knob in place after the first sleeve has been advanced. The rotatable proximal control knob is moveably connected to the second elongate member, and the catheter is configured such that rotation of the rotatable proximal control knob moves the second sleeve in a proximal direction.

Example 2

Another embodiment provides a handle assembly for a delivery catheter having a distal end and a proximal end. The handle assembly includes a first hollow elongate member partially housed within the handle assembly, and a second hollow elongate member partially housed within the handle assembly. The second hollow elongate member is encompassed along at least a portion of its length by the first hollow elongate member, and the first and second hollow elongate members are axially movable with respect to one another. The handle assembly further includes a first rotatable control knob movably connected to the first hollow elongate member. The handle assembly is configured such that rotation of the first rotatable control knob moves the first hollow elongate member in an axial direction. A second rotatable control knob is also provides, and is movably connected to the second hollow elongate member. The handle assembly is configured such that rotation of the rotatable proximal control knob moves the second hollow elongate member in an axial direction. A safety button is included with the handle assembly for locking the second rotatable control knob in a desired position.

Example 3

Another embodiment provides a handle assembly for a delivery catheter having a distal end and a proximal end. The handle assembly includes a main handle having a distal end and a proximal end. A rotatable distal control knob is rotatably connected to the main handle at the distal end of the main handle. The distal control knob includes threads formed on the interior surface thereof. A rotatable proximal control knob is rotatably connected to the main handle proximal to the distal control knob. The proximal control knob includes threads formed on the interior surface thereof. A first elongate member extends from the handle assembly. The first elongate member has a proximal end and a distal end. A second elongate member extends from the handle assembly. The second elongate member has a proximal end and a distal end. A first boss having a tongue for engaging the distal control knob threads is included in the handle assembly. A second boss is also included. The second boss is connected to the first boss and the first elongate member such that axial movement of the first boss results in corresponding axial movement of the second boss. A locking rod is attached to the first boss. A safety button is positioned on the main handle distal of the distal control knob. The safety button has a channel therein configured to receive a portion of the locking rod. A third boss is included. The third boss has a tongue for engaging the proximal control knob threads. The third boss is connected to the second elongate member.

What is claimed is:

1. A prosthetic valve delivery device comprising:
a handle assembly including a handle, a first control member, a locking pin coupled to the first control member, and a safety component, the safety component being configured to be movable relative to the locking pin between an initial position and a secondary position, wherein the safety component is coupled to the handle in the initial position and is coupled to the handle in the secondary position;
a distal tip assembly including a first sleeve; and
a first elongate member extending from the handle assembly, the first elongate member having a proximal end and a distal end and the first sleeve being connected to the distal end of the first elongate member, wherein the first control member is connected to the proximal end of the first elongate member, and
wherein manipulation of the first control member concurrently moves the first sleeve and the locking pin in an axial direction, and
wherein the locking pin is configured to be moveable via manipulation of the first control member from a first position in which the locking pin does not engage the safety component to a second position in which the locking pin engages the safety component and thereby locks the first sleeve in place.

2. The device of claim 1, wherein the safety component includes a recess formed therein, and wherein the safety component is configured to be moveable from the initial position in which the recess of the safety component is not aligned with the locking pin and the locking pin is blocked from being advanced into the recess of the safety component to the secondary position in which the recess of the safety component is aligned with the locking pin and the locking pin is not blocked from being advanced into the recess of the safety component.

3. The device of claim 2, wherein the safety component is biased in the first initial position.

4. The device of claim 2, wherein the safety component is movable in a radial direction.

5. The device of claim 4, wherein the safety component comprises a safety button.

6. The device of claim 2, wherein the safety component is movable in a distal or proximal direction.

7. The device of claim 2, wherein the safety component is movable in a lateral direction.

8. The device of claim 1, further comprising a second elongate member, wherein each of the first elongate member and second elongate member are hollow, and wherein the first elongate member is encompassed along at least a portion of its length by the second elongate member, and wherein the first elongate member and the second elongate member are axially movable with respect to one another.

9. The device of claim 1, wherein the first control member comprises a rotatable control knob.

10. The device of claim 9, wherein the rotatable control knob is rotatable around a longitudinal axis of the handle assembly.

11. The device of claim 1, wherein manipulation of the first control member moves the first sleeve to at least partially release a prosthetic valve at least partially contained within the first sleeve.

12. The device of claim 1, wherein the locking pin is configured to prevent manipulation of the first control member when the locking pin is in the second position.

13. The device of claim 1, wherein the locking pin is disposed within a channel in an interior of the handle assembly.

14. The device of claim 1, wherein the device is configured for transapical delivery of a prosthetic heart valve.

15. The device of claim 1, wherein the device is configured for transfemoral delivery of a prosthetic heart valve.

16. A prosthetic valve delivery device comprising:
a handle assembly including a handle, a first control member, a locking pin coupled to the first control member, and a safety component, the safety component being configured to be movable relative to the locking pin between an initial position and a secondary position, wherein the safety component is coupled to the handle in the initial position and is coupled to the handle in the secondary position;
a distal tip assembly including a first sleeve; and
a first elongate member extending from the handle assembly, the first elongate member having a proximal end and a distal end and the first sleeve being connected to the distal end of the first elongate member, wherein the first control member is connected to the proximal end of the first elongate member, and
wherein manipulation of the first control member concurrently moves the first sleeve and the locking pin in an axial direction, and
wherein the locking pin is configured to be moveable via manipulation of the first control member from a first position in which the locking pin does not engage the safety component to a second position in which the locking pin engages the safety component, the locking pin being configured to prevent manipulation of the first control member when in the second position.

17. The device of claim 16, wherein the safety component includes a recess formed therein, and wherein the safety component is configured to be moveable from the initial position in which the recess of the safety component is not aligned with the locking pin and the locking pin is blocked from being advanced into the recess of the safety component to the secondary position in which the recess of the safety component is aligned with the locking pin and the locking pin is not blocked from being advanced into the recess of the safety component.

18. The device of claim 17, wherein the safety component is movable in a radial direction and is biased in the initial position.

19. The device of claim 16, wherein manipulation of the first control member moves the first sleeve to at least partially release a prosthetic valve at least partially contained within the first sleeve.

20. The device of claim 16, wherein the locking pin is disposed within a channel in an interior of the handle assembly.

* * * * *